(12) United States Patent
Negoro et al.

(10) Patent No.: US 7,956,020 B2
(45) Date of Patent: Jun. 7, 2011

(54) LUBRICANT COMPOSITION, MECHANICAL ELEMENT, AND METHOD FOR PRODUCING TRIAZINE DERIVATIVES

(75) Inventors: Masayuki Negoro, Tokyo (JP); Hiroshi Kawamoto, Minami-ashigara (JP); Ryo Nishio, Kanagawa (JP); Toshiki Taguchi, Tokyo (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 517 days.

(21) Appl. No.: 12/057,730

(22) Filed: Mar. 28, 2008

(65) Prior Publication Data

US 2008/0274920 A1    Nov. 6, 2008

(30) Foreign Application Priority Data

Mar. 29, 2007 (JP) ................. 2007-087350
Sep. 11, 2007 (JP) ................. 2007-235132
Mar. 11, 2008 (JP) ................. 2008-060500

(51) Int. Cl.
  *C07D 251/54* (2006.01)
  *C10M 169/04* (2006.01)
(52) U.S. Cl. ...................... 508/258; 508/257
(58) Field of Classification Search .......... 508/258, 508/257
See application file for complete search history.

(56) References Cited

U.S. PATENT DOCUMENTS

| 3,870,716 A | 3/1975 | Belsky et al. |
| 4,830,263 A | 5/1989 | Dexheimer |
| 2004/0266633 A1* | 12/2004 | Negoro et al. ............ 508/257 |
| 2005/0107268 A1 | 5/2005 | Negoro et al. |
| 2005/0209453 A1 | 9/2005 | Negoro et al. |
| 2007/0054814 A1 | 3/2007 | Negoro et al. |

FOREIGN PATENT DOCUMENTS

| EP | 1266950 A1 | 12/2002 |
| GB | 1239608 | 7/1971 |
| JP | 2002-003876 A | 1/2002 |
| JP | 2002-069472 A | 3/2002 |
| JP | 2004-315703 A | 11/2004 |

* cited by examiner

*Primary Examiner* — Walter D Griffin
*Assistant Examiner* — Frank C Campanell
(74) *Attorney, Agent, or Firm* — Buchanan Ingersoll & Rooney PC

(57) ABSTRACT

A lubricant composition comprising following ingredients (a) and (b) is disclosed.
 (a) at least one compound represented by formula (1)
 (b) at least one compound represented by formula (2)

$$(R-X-)_m-D \qquad (1)$$

(b) at least one compound represented by formula (2)

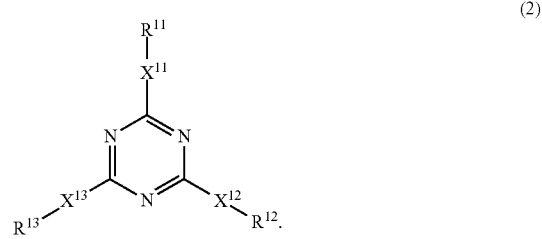

(2)

16 Claims, No Drawings

LUBRICANT COMPOSITION, MECHANICAL ELEMENT, AND METHOD FOR PRODUCING TRIAZINE DERIVATIVES

CROSS-REFERENCE TO RELATED APPLICATIONS

This application claims benefit of priority under 35 U.S.C. 119 to Japanese Patent Application Nos. 2007-087350 filed on Mar. 29, 2007, 2007-235132 filed on Sep. 11, 2007 and 2008-060500 filed on Mar. 11, 2008, and the entire contents of the applications are incorporated herein by reference.

BACKGROUND OF THE INVENTION

1. Field of the Invention

The present invention relates to a lubricant composition to be supplied to mechanical friction sliding members, which is excellent in low friction properties, in wear resistance under extreme pressure and high shearing stress, and in sustainability of such properties. The present invention also relates to a method for producing triazine derivatives.

2. Related Art

Performances required for lubricant relate to that it should be able to lower friction coefficient at mechanical friction sliding members over a wide temperature range and pressure range, and that such effects are sustained as long as possible. It is also expected for the lubricant to not only improve lubricating properties between mechanical friction sliding members, but also to thereby provide wear resistance to such friction sliding members in themselves. Effects, which is brought about by lubricant such as engine oil, of reducing friction coefficient of the friction sliding members and increasing service life thereof directly result in improved fuel cost for mechanical driving, or in other words, energy saving. Elongation of the service life of engine oil not only ensures reduction in waste oil but also reduction in $CO_2$ emission, so that it will be desirable in terms of environmental compatibility which has increasingly been attracting recent public attention. As for bearings or gears, which operate under particularly severe frictional conditions among various sliding members for use in industrial machines, use of conventional lubricant such as lubricating oil or grease may result in film breakage or sticking of the lubricant under particularly severe lubricating conditions, which makes it difficult to obtain a desired low friction coefficient due to abrasion scars. This sometimes lowers the reliability of apparatus, and tends to increase severity of the friction conditions especially for the case that the apparatus is to be downsized, which has been one reason for preventing the apparatus from being downsized. So that there has been a strong demand for a lubricant which can bring about the effects even under severe conditions, can contribute to downsizing of the apparatus, and is excellent in energy saving property.

Lubricants which have previously been used are generally such that comprising a lubricant base oil as a major component, and a lubricant aids such as an organic compound blended thereto. A composition, comprising soft base oil (e.g., synthetic base oil and mineral base oil) and viscosity index improver capable of compensating for too much softness of base oil, is proposed in JPA No. 2002-3876 as lubricant oil to be used in an internal combustion, exhibiting both low friction and anti-wear properties.

Any lubricant compositions without any environmental toxin or pollutant such as heavy metal elements, phosphate compounds and sulfides, exhibiting excellent properties and maintaining the properties for a long term, have not been proposed yet.

In JPA Nos. 2002-69472 and 2004-315703, lubricant compositions comprising a triazine-ring-containing compound, which exhibit low friction properties, are disclosed.

SUMMARY OF THE INVENTION

In the technical field, lubricants have been recently required to exhibit higher performances and to exhibit such performances over a wide range of temperature.

One object of the present invention is to provide a lubricant composition exhibiting good performances even without base oil.

Another object of the invention is to provide a lubricant composition, to be used between sliding surfaces, exhibiting low-friction and anti-wear properties for a long time, even under extreme pressure.

Another object of the invention is to provide a lubricant composition, exhibiting good performances over a wide range of temperature, of which range of service temperature is wide.

Another object of the invention is to provide a lubricant composition without any heavy metal elements, phosphate compounds and sulfides, which are poor in environmentally-compatibility, exhibiting both of long operating life and high environmental compatibility.

Another object of the invention is to provide a long-life mechanical element employing the lubricant composition lubricant composition.

Another object of the invention is to provide a method for producing triazine derivatives which are useful in preparation of lubricant compositions.

In one aspect, the present invention provides a lubricant composition comprising following ingredients (a) and (b):

(a) at least one compound represented by formula (1)

$$(R-X-)_m-D \qquad (1)$$

where "D" represents an m-valent cyclic group capable of bonding to "m" of —X—R; X each independently represents a single bond or a bivalent linking group selected from the group consisting of NH, an oxygen atom, a sulfur atom, carbonyl, sulfonyl and any combinations thereof; R each independently represents a substituted or non-substituted alkyl group, alkenyl group, alkynyl group, aryl group orheterocyclic group, or a halogen atom, hydroxy, amino, mercapto, cyano, sulfide, carboxy or a salt thereof, sulfo or a salt thereof, hydroxyamino, ureido or urethane; and m is an integer from 2 to 11;

(b) at least one compound represented by formula (2)

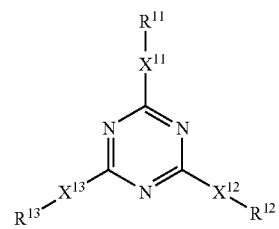

where $X^{11}$, $X^{12}$ and $X^{13}$ each independently represent a single bond or a bivalent linking group selected from the group consisting of $NR^a$(where $R^a$ is a hydrogen atom or a $C_{1-30}$ alkyl group), an oxygen atom, a sulfur atom, carbonyl, sulfonyl and any combinations thereof, provided that at least one of $X^{11}$, $X^{12}$ and $X^{13}$ represents $NR^b$ (where $R^b$ represents a $C_{1-30}$ alkyl group); and $R^{11}$, $R^{12}$ and $R^{13}$ each independently a substituted or non-substituted alkyl group, alkenyl group, alkynyl group, aryl group or heterocyclic group.

In formula (1), "D" may be a cyclic group represented by any one of formulae [1] to [74]:

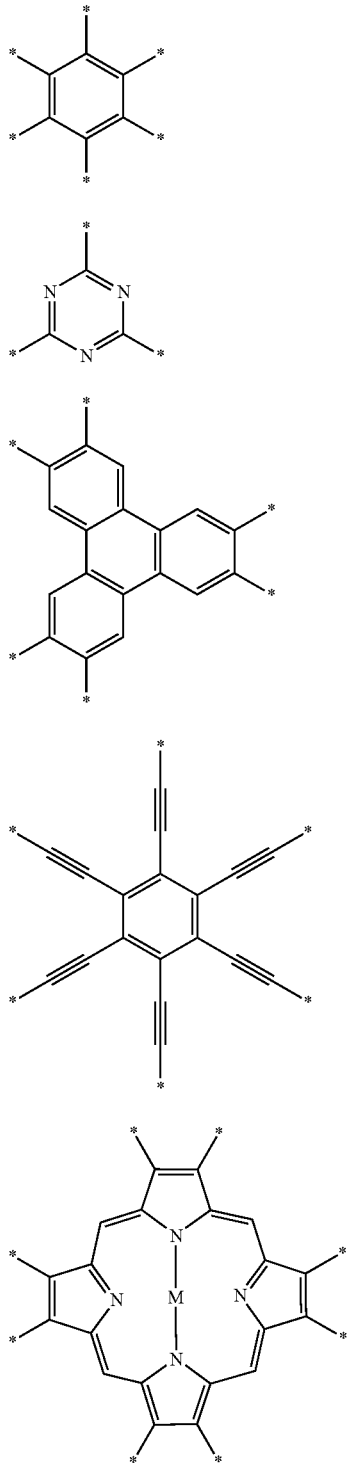

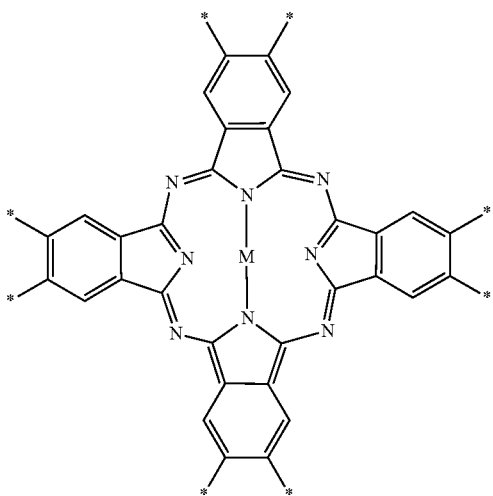

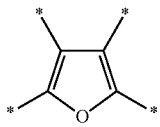

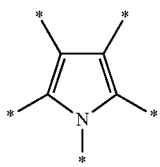

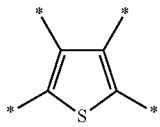

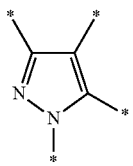

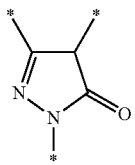

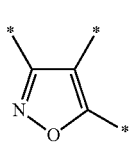

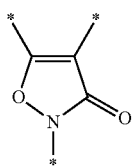 [13]
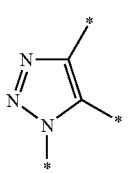 [14]
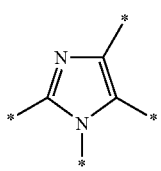 [15]
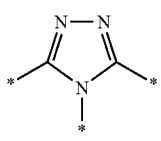 [16]
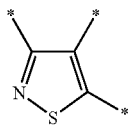 [17]
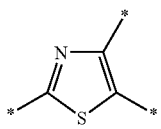 [18]
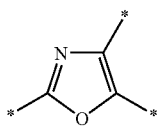 [19]
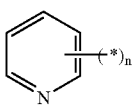 [20]
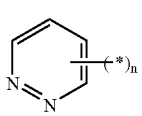 [21]
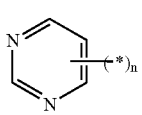 [22]
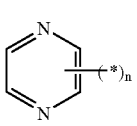 [23]
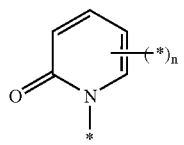 [24]
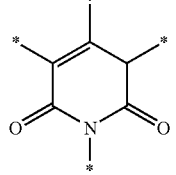 [25]
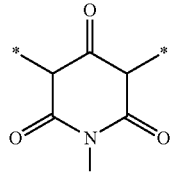 [26]
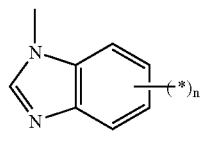 [27]
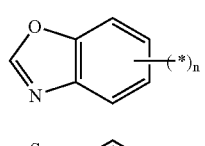 [28]
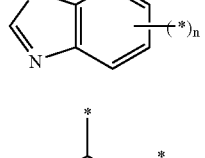 [29]
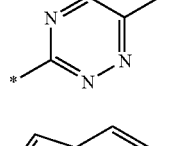 [30]
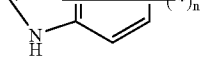 [31]
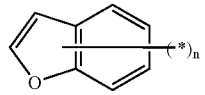 [32]
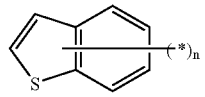 [33]
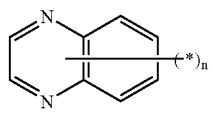 [34]

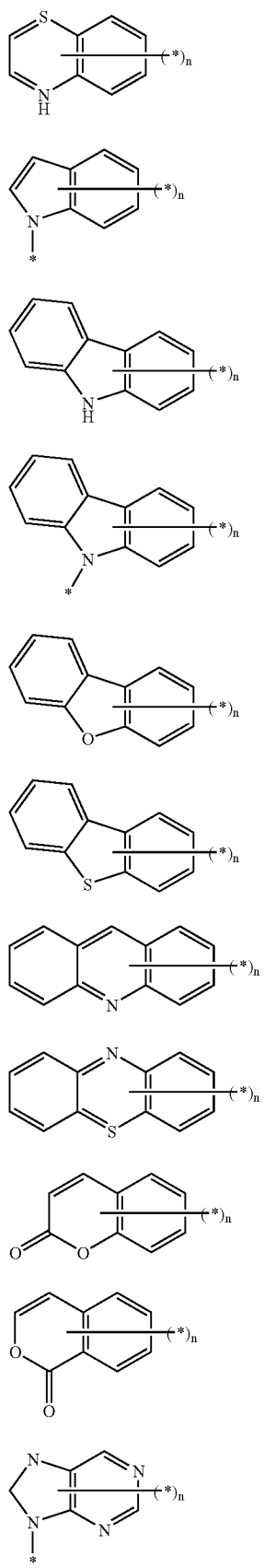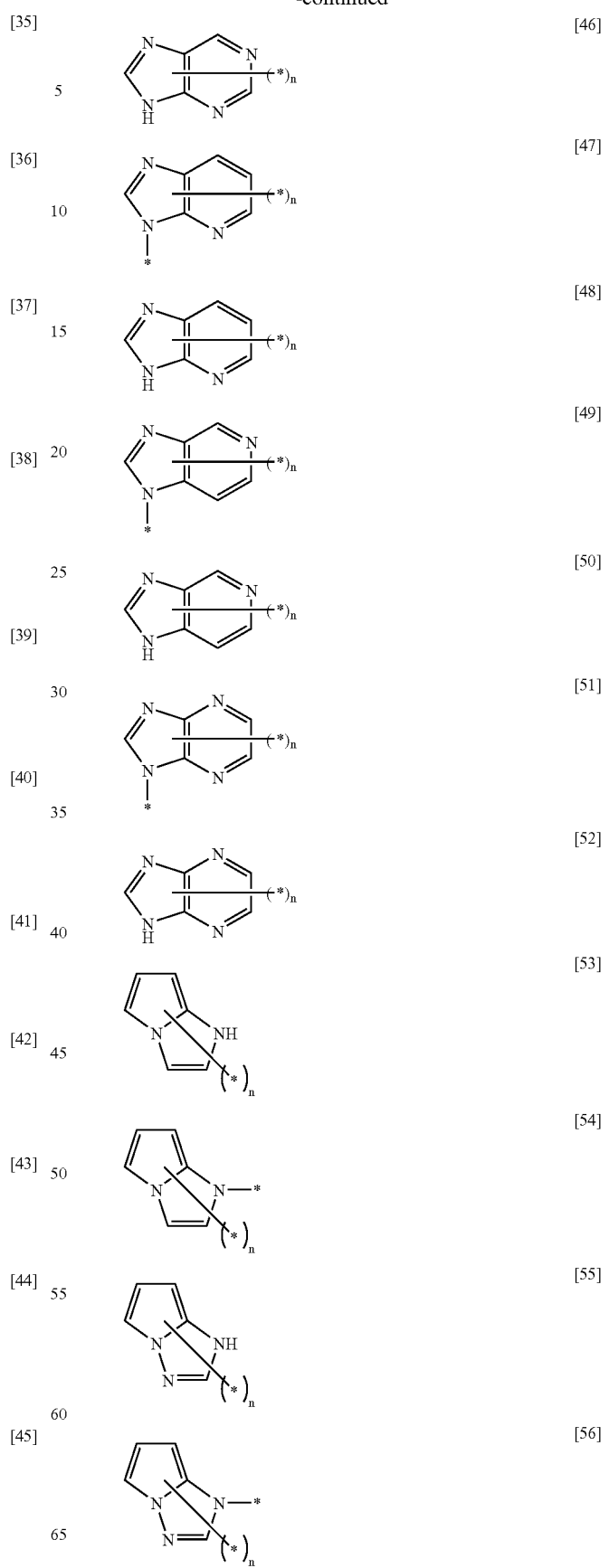

[57] 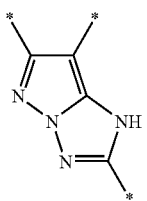
[58] 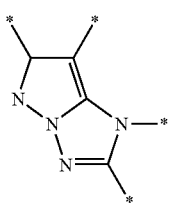
[59] 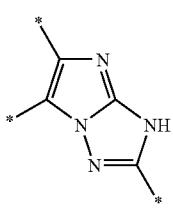
[60] 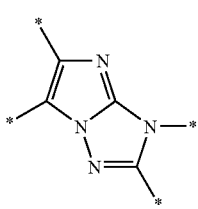
[61] 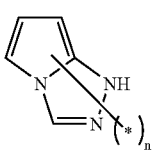
[62] 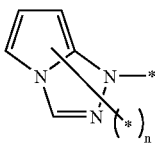
[63] 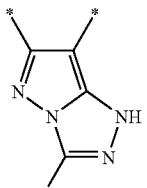
[64] 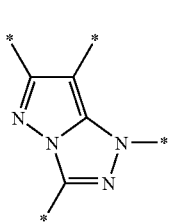
[65] 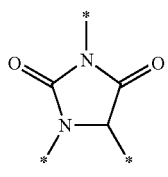
[66] 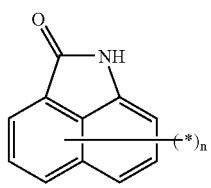
[67] 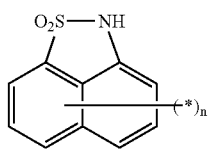
[68] 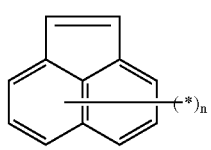
[69] 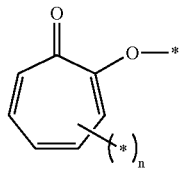
[70] 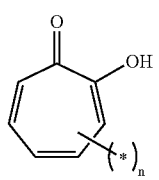
[71] 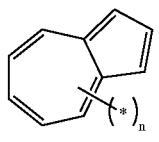
[72] 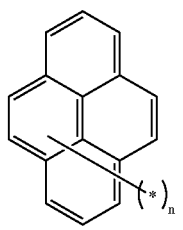

-continued

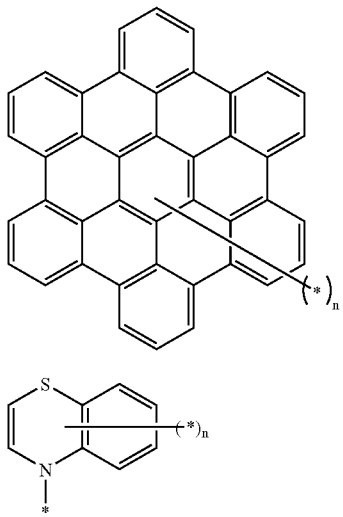

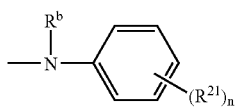

where n is a integer equal to or more than 2; each * in the formulae means a site bindable with a side chain, provided that all portions indicated with * are not necessary to bind to a side chain; and M represents a metal ion or two hydrogen atoms.

In formula (1), "D" may be a 5-, 6- or 7-membered heterocyclic ring residue.

In formula (2), at least one of $R^{11}$—$X^{11}$, $R^{12}$—$X^{12}$ and $R^{13}$—$X^{13}$ may be a group represented by formula (3):

$$\begin{array}{c} R^b \\ | \\ -N-\phantom{x}\phantom{x}(R^{21})_n \end{array} \qquad (3)$$

where $R^b$ represents a $C_{1-30}$ alkyl group; $R^{21}$ represents a substituted or non-substituted alkyl group, alkenyl group, alkynyl group, aryl group or heterocyclic group; and n is an integer from 1 to 5.

In formula (3), $R^b$ may be a $C_{1-30}$ alkyl group.

As embodiments of the invention, there are provided the lubricant composition comprising 5.0 to 90.0% by mass of said ingredient (a) and 10.0 to 95.0% by mass of said ingredient (b); and the lubricant composition comprising two or more compounds represented by formula (2).

In another aspect, the present invention provides a mechanical element comprising at least two surfaces movable at peripheral speeds differed from each other, and the lubricant composition disposed between said two surfaces; and a method for reducing friction between two surfaces, comprising providing the lubricant composition to a gap between two faces.

In another aspect, the present invention provides a method for producing the lubricant composition comprising:
producing a mixture of at least two kinds of compounds represented by formula (1) as ingredient (a) and/or a mixture of at least two kinds of compounds represented by formula (2) as ingredient (b); and mixing ingredients (a) and (b).

In the method, at least one of ingredients (a) and (b) may be produced as a mixture of at least two kinds of compounds represented by formula (1) or (2) according to a reaction employing at least two kinds of reagents.

In the method, at least one of ingredients (a) and (b) may be produced according to an addition reaction of ethylene oxide or propylene oxide gas, which has a chain length distribution, as a mixture of at least two kinds of compounds represented by formula (1) or (2).

The present invention also provides the lubricant composition, wherein ingredient (a) is a mixture of at least two kinds of compounds represented by formula (1), which have a substituent as at least one of substituents R containing a repeating unit of ethylene oxy (—$CH_2CH_2O$—) or propylene oxy (—$CH_2CH_2CH_2O$—), of which repeating numbers of the unit are different among said at least two kinds of compounds represented by formula (1); and/or ingredient (b) is a mixture of at least two kinds of compounds represented by formula (2), which have a substituent as at least one of substituents $R^{11}$, $R^{12}$ and $R^{13}$ containing a repeating unit of ethylene oxy (—$CH_2CH_2O$—) or propylene oxy (—$CH_2CH_2CH_2O$—), of which repeating numbers of the unit are different among said at least two kinds of compounds represented by formula (2).

The present invention also provides a method for producing a mixture of at least two kinds of compounds represented by formula (1):

$$(R-X-)_m-D \qquad (1)$$

where "D" represents an m-valent cyclic group capable of bonding to "m" of —X—R; X each independently represents a single bond or a bivalent linking group selected from the group consisting of NH, an oxygen atom, a sulfur atom, carbonyl, sulfonyl and any combinations thereof; R each independently represents a substituted or non-substituted alkyl group, alkenyl group, alkynyl group, aryl group or heterocyclic group, or a halogen atom, hydroxy, amino, mercapto, cyano, sulfide, carboxy or a salt thereof, sulfo or a salt thereof, hydroxyamino, ureido or urethane, provided that at least one of R is a substituent containing a repeating unit of ethylene oxy (—$CH_2CH_2O$—) or propylene oxy (—$CH_2CH_2CH_2O$—); and m is an integer from 2 to 11;

comprising carrying out addition reaction of ethylene oxide or propylene oxide gas which has a chain length distribution, thereby to form a mixture of at least two kinds of compounds represented by formula (1), which have a substituent containing a repeating unit of ethylene oxy (—$CH_2CH_2O$—) or propylene oxy (—$CH_2CH_2CH_2O$—), of which repeating numbers of the unit are different among said at least two kinds of compounds.

The present invention also provides a method for producing a mixture of at least two kinds of compounds represented by formula (2):

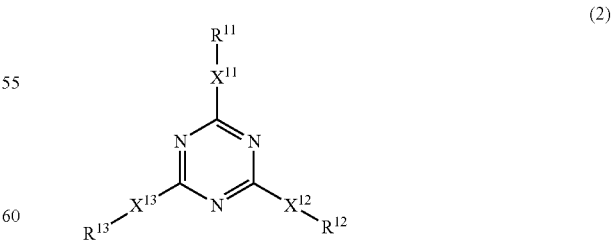

where $X^{11}$, $X^{12}$ and $X^{13}$ each independently represent a single bond or a bivalent linking group selected from the group consisting of $NR^a$ (where $R^a$ is a hydrogen atom or a $C_{1-30}$ alkyl group), an oxygen atom, a sulfur atom, carbonyl, sulfonyl and any combinations thereof, provided that at least one of $X^{11}$, $X^{12}$ and $X^{13}$ represents $NR^b$ (where $R^b$ represents a $C_{1-30}$ alkyl group); and $R^{11}$, $R^{12}$ and $R^{13}$ each independently a substituted or non-substituted alkyl group, alkenyl group, alkynyl group, aryl group or heterocyclic group, provided that at least one of $R^{11}$, $R^{12}$ and $R^{13}$ is a substituent containing a repeating unit of ethylene oxy (—$CH_2CH_2O$—) or propylene oxy (—$CH_2CH_2CH_2O$—);

comprising carrying out addition reaction of ethylene oxide or propylene oxide gas which has a chain length distribution, thereby to form a mixture of at least two kinds of compounds represented by formula (2), which have a substituent containing a repeating unit of ethylene oxy (—$CH_2CH_2O$—) or propylene oxy (—$CH_2CH_2CH_2O$—), of which repeating numbers of the unit are different among said at least two kinds of compounds.

In another aspect, the present invention provides a method for producing a compound represented by formula (2):

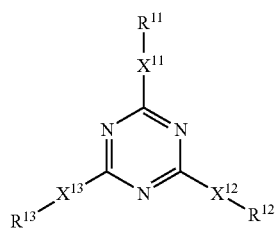

(2)

where $X^{11}$, $X^{12}$ and $X^{13}$ each independently represent a single bond or a bivalent linking group selected from the group consisting of $NR^a$ (where $R^a$ is a hydrogen atom or a $C_{1-30}$ alkyl group), an oxygen atom, a sulfur atom, carbonyl, sulfonyl and any combinations thereof, provided that at least one of $X^{11}$, $X^{12}$ and $X^{13}$ represents $NR^b$ (where $R^b$ represents a $C_{1-30}$ alkyl group); and $R^{11}$, $R^{12}$ and $R^{13}$ each independently a substituted or non-substituted alkyl group, alkenyl group, alkynyl group, aryl group or heterocyclic group;

comprising carrying out reaction of trichloro-, dichloro- or monochloro-triazine and amine and/or aminophenol by adding aqueous solution of sodium acetate to a reaction system.

In the method, at least one of $R^{11}$—$X^{11}$, $R^{12}$—$X^{12}$ and $R^{13}$—$X^{13}$ in formula (2) may be a group represented by formula (3):

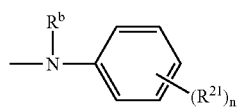

(3)

where $R^b$ represents a $C_{1-30}$ alkyl group; $R^{21}$ represents a substituted or non-substituted alkyl group, alkenyl group, alkynyl group, aryl group or heterocyclic group; and n is an integer from 1 to 5.

DETAILED DESCRIPTION OF THE INVENTION

The invention is described in detail hereinunder. The expression "from a lower value to an upper value" referred herein means that the range intended by the expression includes both the lower value and the upper value.

[Lubricant Composition]

One feature of the lubricant composition of the present invention resides in comprising following ingredients (a) and (b). By comprising both of ingredients (a) and (b), the lubricant composition of the invention can form a lubricant membrane capable of enduring load in the vertical direction between the sliding faces, and is excellent in sliding properties in the sliding direction. Further, the lubricant composition of the invention exhibits superior lubricant properties at a relatively low temperature, compared with ingredient (a) or (b) alone.

In general, a lubricant is required to form oil membranes on sliding faces, continue to form them and exhibit low-friction properties, and in order to achieve such performances, effective molecular orientation at sliding faces is required. In terms of high molecular orientation, in general, it may be considered that using ingredient (a) or (b) as single agent is preferred to using them in combination. However, the lubricant composition of the invention, comprising both ingredients (a) and (b), can form oil membranes without any disorder. The lubricant composition of the invention is not only excellent in ability of forming oil membranes but also excellent in lubrication properties at a relatively low temperature compared with ingredient (a) or (b) alone, and such effect of the invention is unexpected.

Each of ingredients employable will be described in detail below.

Ingredient (a)

Ingredient (a) consists one or more selected from the compounds represented by formula (1) shown below.

$$(R-X-)_m-D \qquad \text{Formula (1)}$$

In the formula, "D" represents an m-valent cyclic group capable of bonding to "m" of —X—R; X each independently represents a single bond or a bivalent linking group selected from the group consisting of NH, an oxygen atom, a sulfur atom, carbonyl, sulfonyl and any combinations thereof; R each independently represents a substituted or non-substituted alkyl group, alkenyl group, alkynyl group, aryl group or heterocyclic group, or a halogen atom, hydroxy, amino, mercapto, cyano, sulfide, carboxy or a salt thereof, sulfo or a salt thereof, hydroxyamino, ureido or urethane; and m is an integer from 2 to 11.

The compound represented by formula (1) has a cyclic group "D" and "m"s (m is an integer from 2 to 11) side chains "(R—X—)" bonding to the cyclic group. Discotic compounds are preferred. In this specification, the "discotic compound" means a compound having a discotic structure at least as a partial structure thereof, without needing that the structure of the whole molecule is discotic. The structural feature of the discotic segment can be explained with an original form thereof, namely a hydrogenised compound, as an example, as follows:

A molecular size of a hydrogenised compound, which can be an original form of a discotic compound, may be obtained by 1) to 5) steps.

1) To create a possible planar, desirably an exact planar, molecule structure for a target molecule. For creating, standard bond-length and bond-angle values based on orbital hybridization are desirably used, and such standard values can be obtained with reference to the 15th chapter in the second volume of "Chemical Handbook, revised version 4, Foundation Section (Kagaku Binran Kaitei 4 Kisohen)" compiled by The Chemical Society of Japan, published by MARUZEN in 1993.

2) To optimize a molecular structure using the above-obtained planar structure as a default by molecular orbital method or molecular mechanics method. Examples of such methods include Gaussian92, MOPAC93, CHARMm/QUANTA and MM3, and Gaussian92 is desirably selected.

3) To move a centroid of the optimized structure to an origin position and to create a coordinate having an axis equal to a principal axis of inertia (a principal axis of a inertia tensor ellipsoid).

4) To set a sphere defined by van der Waals radius in each atom positions thereby drawing a molecular structure.

5) To calculate lengths along to three coordinate axes on van der Waals surface thereby obtaining "a", "b" and "c".

Using "a", "b" and "c" obtained trough the steps 1) to 5) "a discotic structure" can be defined as a structure which satisfies $a \geq b > c$ and $a \geq b \geq a/2$, and a preferred example of the discotic structure is a structure which satisfying $a \geq b > c$ and $a \geq b \geq 0.7a$ or $b/2 > c$.

Examples of the compound, which can be an original form of a discotic compound, include mother cores and derivatives described in various literatures such as "Ekisho no Kagaku (Science of Liquid Crystal), edited by the Chemical Society of Japan, Seasonal Chemical Review No. 22, Chapter 5, and Chapter 10, Section 2 (1994); C. Destrade et al., Mol. Crysr. Liq. Cryst., vol. 71, p. 111 (1981); B. Kohne et al., Angew. Chem. Vol. 96, p. 70; compounds described in J. M. Lehn et al., J. Chem. Soc. Chem. Commun., p. 1794 (1985); and J. Zhang et al., J. Am. Chem. Soc., vol. 116, p. 2655 (1994). More specific examples of the hydrogenated compound include benzene derivatives, tri phenylene derivatives, truxene derivatives, phthalocyanine derivatives, porphyrin derivatives, anthracene derivatives hexaethynylbenzene derivatives, dibenzopyrene derivatives, coronene derivatives and phenylacetylene macrocycl derivatives. The examples also include cyclic compounds described in "Chemical Review (Kagaku Sousetsu) No. 15 Chemistry of Novel Aromatic Series (Atarashii Houkouzoku no Kagaku)" compiled by the Chemical Society of Japan, published by University of Tokyo Press in 1977; and electronic structures such as heteroatom-substituted compounds thereof.

Examples of the cyclic group represented by D include aryl groups and heterocyclic groups. Examples of the aryl rings in the aryl group include a benzene ring, an indene ring, a naphthalene ring, a triphenylene ring, a fluorine ring, a phenanthrene ring, an anthracene ring and a pyrane ring. The aryl group may have at least one substituent.

The heterocyclic group is desirably selected from 5-, 6- or 7-membered heterocyclic groups, more desirably from 5- or 6-membered heterocyclic groups, and much more desirably from 6-membered heterocyclic groups. One or more hetero atoms embedded in the heterocyclic ring are desirably selected from the group consisting of nitrogen, oxygen and sulfur atoms. Aromatic heterocyclic rings are preferred. An aromatic heterocyclic ring usually belongs to unsaturated heterocyclic rings, and the heterocyclic group is more desirably selected from unsaturated heterocyclic groups having maximum double bondings. Examples of the heterocyclic ring include furan ring, thiophene ring, pyrrole ring, pyrrolidine ring, oxazole ring, isoxazole ring, thiazole ring, isothiazole ring, imidazole ring, imidazoline ring, imidazolidine ring, pyrazole ring, pyrazoline ring, pyrazolidine ring, triazole ring, furazan ring, tetrazole ring, pyrane ring, thyine ring, pyridine ring, piperidine ring, oxazine ring, morpholine ring, thiazine ring, pyridazine ring, pyrimidine ring, pyrazine ring, piperazine ring and triazine ring. Triazine ring is preferred and 1,3,5-triazine ring is more preferred. The heterocyclic ring may be condensed with other heterocyclic ring, or at least one aliphatic ring or aryl ring. However monocyclic heterocyclic groups are preferred.

Preferable Examples of "D" include groups [1] to [74] shown below.

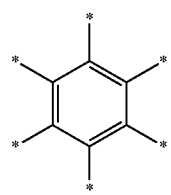

[1]

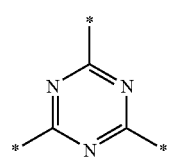

[2]

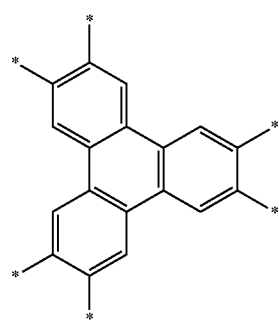

[3]

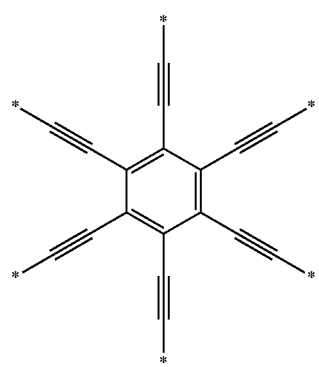

[4]

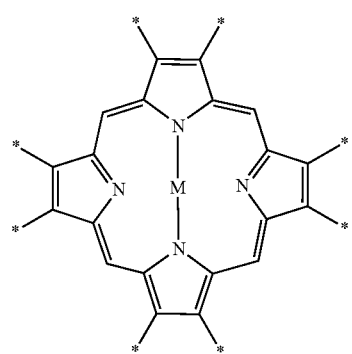

[5]

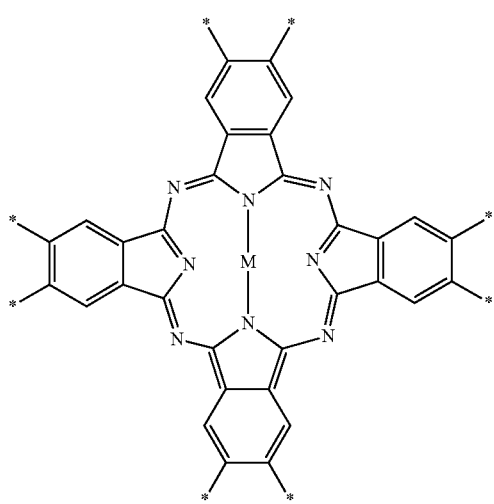
[6]
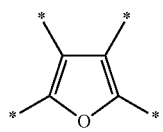
[7]
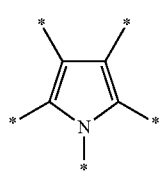
[8]
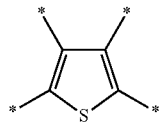
[9]
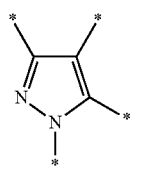
[10]
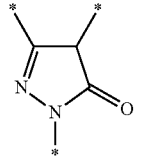
[11]
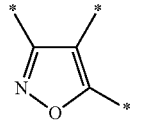
[12]
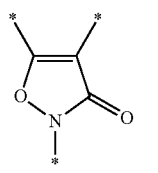
[13]
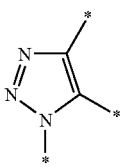
[14]
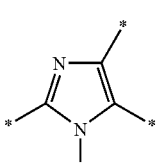
[15]
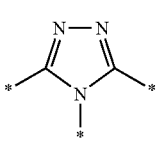
[16]
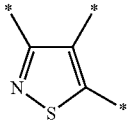
[17]
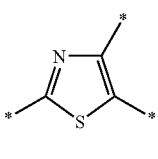
[18]
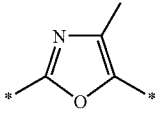
[19]
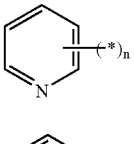
[20]
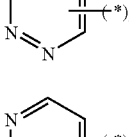
[21]
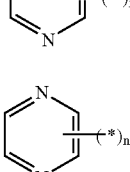
[22]
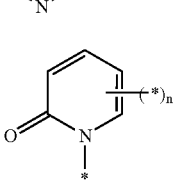
[23]
[24]

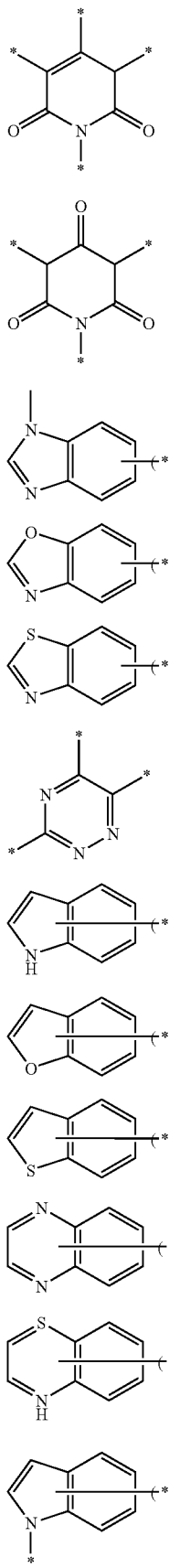
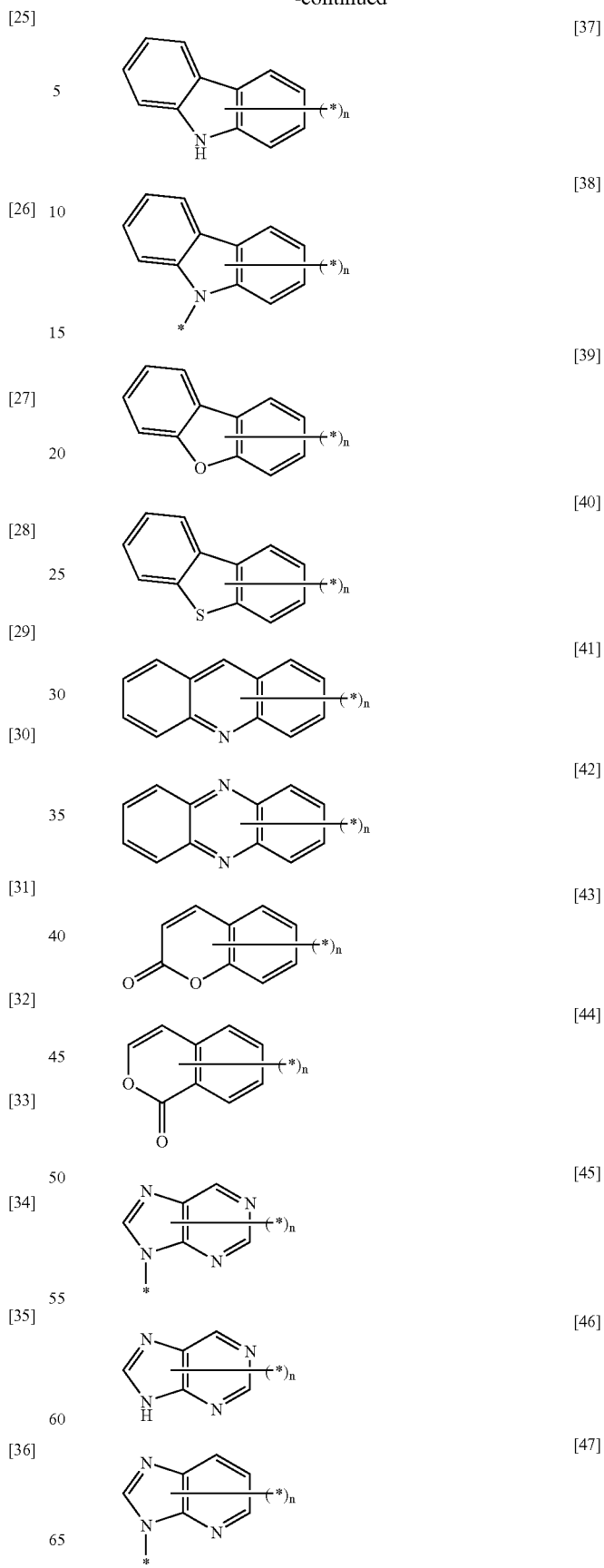

[48] 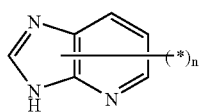
[49] 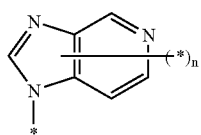
[50] 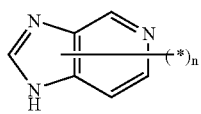
[51] 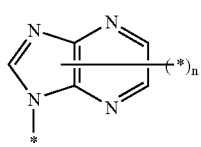
[52] 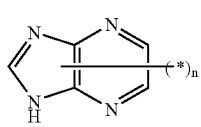
[53] 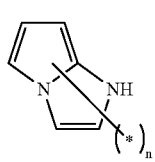
[54] 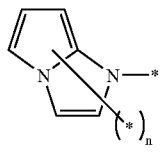
[55] 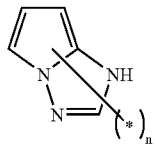
[56] 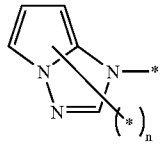
[57] 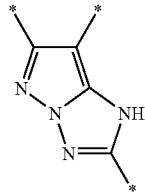
[58] 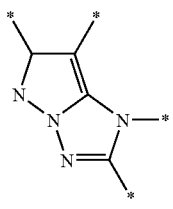
[59] 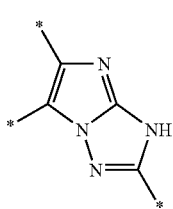
[60] 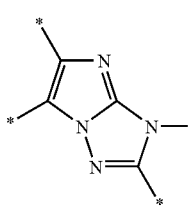
[61] 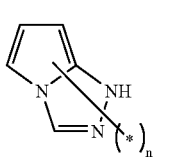
[62] 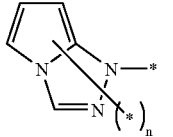
[63] 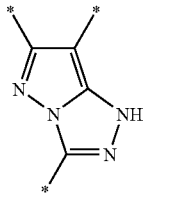
[64] 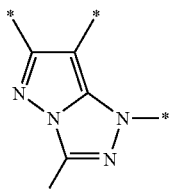
[65] 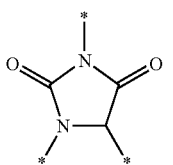

-continued

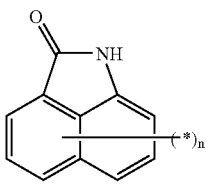

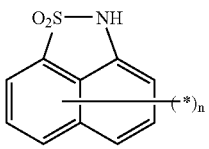

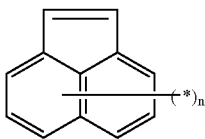

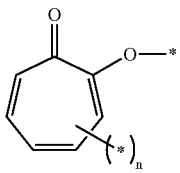

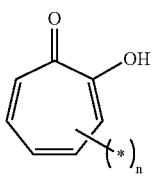

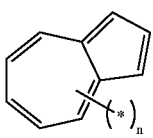

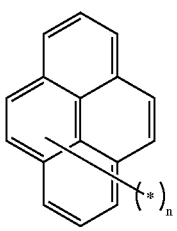

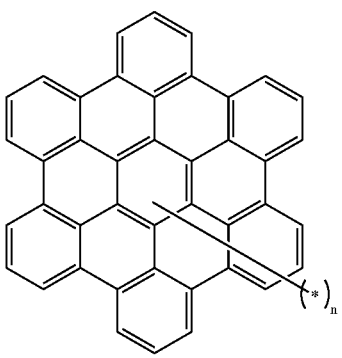

-continued

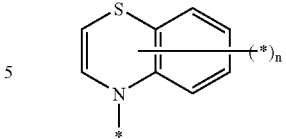

In the formulae, n is an integer equal to or more than 2; each * in the formulae means a site bindable with a side chain, provided that all portions indicated with * are not necessary to bind to a side chain; and M represents a metal ion or two hydrogen atoms.

The mother core is preferably selected from pi-conjugated system cores containing at least one polar element, and groups [1], [2], [3], [6], [10], [11], [20], [22], [27] and [56] are preferred: among these, groups [1], [2], [3], [6], [10] and [20] are more preferred; and, especially, groups [1], [2] and [3] are even more preferred.

In the formula (1), X each represents a single bond or a bivalent linking group selected from the group consisting of NH, oxygen, sulfur, carbonyl, sulfonyl and any combinations thereof. When X is a single bond, X may bond directly to nitrogen atom, having free atomic valence, of a heterocyclic ring such as a piperidine ring or may bond to a heteroatom not having free atomic valence to form an onium salt such as an oxonium salt, sulfonium salt or ammonium salt. X desirably represents a sulfur atom or NH.

When R represents an alkyl group, the alkyl group is desirably selected from $C_{1-40}$ alkyl groups, more desirably from $C_{2-30}$ alkyl groups, much more desirably from $C_{4-30}$ alkyl groups and further much more desirably from $C_{6-30}$ alkyl groups. The alkyl group may have a linear or branched chain structure and may be substituted or non-substituted. Examples of the substituent include halogen atoms, alkoxy groups (preferably $C_{1-40}$ and more preferably $C_{1-20}$ alkoxy groups such as methoxy, ethoxy, methoxyethoxy or phenoxy), alky- or aryl-thio groups (preferably $C_{1-40}$ and more preferably $C_{1-20}$ alkyl thio groups such as methylthio, ethylthio and propylthio; and preferably $C_{6-40}$ and more preferably $C_{6-20}$ arylthio groups such as phenylthio), alkylamino groups (preferably $C_{1-40}$ and more preferably $C_{1-20}$ alkyl amino groups such as methylamino and propylamino), acyl groups (preferably $C_{1-40}$ and more preferably $C_{2-20}$ acyl groups such as acetyl, propanoyl, octanoyl and benzoyl), acyloxy groups (preferably $C_{1-40}$ and more preferably $C_{2-20}$ acyloxy groups such as acetoxy, pivaloyloxy and benzoylox), hydroxyl, mercapto, amino, carboxyl, sulfo, carbamoyl, sulfamoyl, and ureido.

When R represents an alkenyl or alkynyl group, the alkenyl or alkynyl group is desirably selected from $C_{2-40}$ alkenyl or alkynyl groups, more desirably from $C_{2-30}$ alkenyl or alkynyl groups, much more desirably from $C_{4-30}$ alkenyl or alkynyl groups and further much more desirably from $C_{6-30}$ alkenyl or alkynyl groups. The alkenyl or alkynyl group may have a linear or branched chain structure and may be substituted or non-substituted with one or more of those exemplified as the substituent group of the alkyl group.

Examples of the aryl group represented by R include phenyl, indenyl, α-naphthyl, β-naphthyl, fluorenyl, phenanthryl, anthracenyl and pyrenyl, and phenyl and naphthyl are preferred. The aryl group may be substituted or non-substituted. Examples of the substituent group include those exemplified above as a substituent group for the alkyl group, and $C_{1-40}$ alkyl groups. The substituent group for the aryl group is desirably selected from substituents having a $C_8$ or longer linear or branched alkyl group, and preferred examples of such substituent include alkyl groups such as octyl, decyl, hexadecyl or 2-ethylhexyl; alkoxy groups such as dodecyloxy or hexadecyloxy; sulfide groups such as hexadecylthio; substituted amino groups such as heptadecylamino; octylcarbamoyl, octanoyl and decylsulfamoyl. The aryl group desirably has two or more substituent groups selected from these. And the aryl group may also be substituted by other substituent groups such as a halogen atom, hydroxyl, cyano, nitro, carboxyl, sulfo or the like, besides the foregoing substituents.

When R represents a heterocyclic group, the heterocyclic group is preferably selected from five- to seven-membered heterocyclic groups, more preferably selected from five- or six-membered groups, and most preferably selected from six-membered groups, similarly to D. Specific examples of such skeletons can be found in heterocyclic rings listed in "Iwanami Rikagaku Jiten (Iwanami's Physicochemical Dictionary; Iwanami Shoten, Publishers), the 3rd edition, supplement Chapter 11 "Nomenclature for Organic Chemistry", Table 4 "Names of Principal Hetero Monocyclic Compounds" on page 1606, and Table 5 "Names of Principal Condensed Heterocyclic Compounds" on page 1607. The heterocyclic groups are, similarly to the foregoing aryl group, preferably substituted with a substituent containing a $C_{8-30}$ linear or branched alkyl chain, where substitution by two or more groups is more preferable. Specific examples of the substituent containing such chain are same as those described in the above. The heterocyclic group may also be substituted by halogen atom, hydroxyl, cyano, nitro, carboxyl, sulfo or the like, besides the foregoing substituents.

Preferably, at least one of Rs in formula (1) contains an ester bond; and more preferably, at least one of Rs is an alkoxy group having at least one substituent containing a linear or branched alkyl residue having an ester bond therein. Even more preferably, all of Rs in formula (1) contain an ester bond; and even much more preferably, all of Rs are alkoxy groups having at least one substituent containing a linear or branched alkyl residue having an ester bond therein.

Preferably, at least one of m's R (occasionally referred to as "side chain" hereinafter) contains a group represented by formula (4a) or (4b). It is noted that the left end ($—X^0$) of the group shown below is the "X" side.

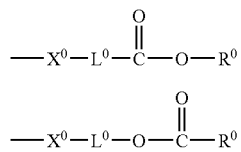

(4a)

(4b)

In the formulae, $X^0$ represents a single bond or a bivalent linking group selected from the group consisting of $NR^1$, where $R^1$ is a hydrogen atom or $C_{1-30}$ alkyl group, oxygen, sulfur, carbonyl, sulfonyl or any combinations thereof.

In the formulae, $L^0$ represents a bivalent linking group selected from the group consisting of an alkylene group, $NR^1$, where $R^1$ is a hydrogen atom or $C_{1-30}$ alkyl group, oxygen, sulfur, carbonyl, sulfonyl or any combinations thereof. The bivalent linking group may be substituted or non-substituted. In the specification, the term of "alkylene group" is used for not only any chain alkylene groups but also any cycloalkylene groups. $L^0$ is desirably selected from alkylene groups.

Preferred examples of the combination of $X^0$ and $L^0$, namely $—X^0$-$L^0$-, include $—O(C=O)$-alkylene- and $—O(C=O)$-cycloalkylene-.

$R^0$, which is located at the end of the side chain, represents a substituted or non-substituted alkyl group or aryl group.

The compound is more desirably selected from the compounds in which at least one of the side chains contains the group represented by the formula (4a). Among these, when the compound in which at least one of the side chains contains the group represented by the formula (4) is used, both of low friction coefficient and low viscosity can be obtained. It is noted that the left end, namely $-L^{01}$, bonds to the cyclic group "D".

Formula (4):

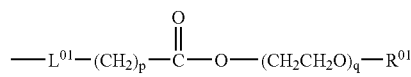

In the formula, $L^{01}$ has the same meaning of $X^0$. $L^{01}$ is desirably selected from the group consisting of oxygen, sulfur, $—(C=O)O—$ and $—NH—(C=O)O—$. $R^{01}$ is a substituted or non-substituted $C_{1-30}$ alkyl group; and P and q respectively represent an integer. $R^{01}$ is desirably selected from substituted or non-substituted $C_{1-25}$ alkyl groups, and more desirably selected from $C_{1-20}$ alkyl groups. Examples of the substituent group for the alkyl group include halogen atoms, alkoxy groups such as methoxy, ethoxy, methoxyethoxy or phenoxy; sulfide groups such as methylthio, ethylthio or propylthio; alkylamino groups such as methylamino or propylamino; acyl groups such as acetyl, propanoyl, octanoyl or benzoyl; acyloxy groups such as acetoxy, pivaloyloxy or benzoyloxy; aryl groups, heterocyclic groups, hydroxyl, mercapto, amino, cyano, nitro, carboxyl, sulfo, carbamoyl, sulfamoyl and ureido. P is desirably an integer selected from 1 to 20, and more desirably selected from 2 to 10. In the formula, q is desirably an integer selected from 1 to 10, and more desirably selected from 1 to 5.

It is also preferable that at least one of he side chains contains a group represented by formula (5). It is to be noted that the left end ($-L^{01}$) is located at the cyclic group "D" side.

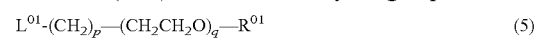 (5)

In the formula, the definitions of $L^{01}$, $R^{01}$, p and q are same as those in formula (4) respectively, and their preferred ranges are same those in formula (4) respectively.

It is also preferable that at least one of he side chains contains a group represented by formula (6) or (7).

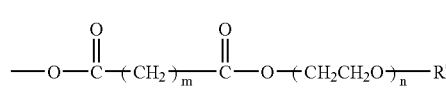 (6)

In the formula, $R^{01}$ represents a substituted or non-substituted $C_{1-30}$ alkyl group; and m and n respectively represent an integer. The definition and the preferred range of $R^{01}$ are same as those in formula (4).

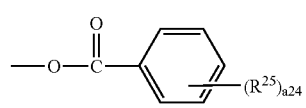 (7)

In the formula, $R^{25}$ represents a substituent group and a24 is an integer from 1 to 5.

Examples of the substituent represented by $R^{25}$, $R^{71}$ or $R^{72}$ in the formulae include halogen atoms such as fluorine, chlorine and bromine atoms; alkyl groups (preferably $C_{1-40}$ and more preferably $C_{1-20}$ alkyl groups) such as methyl, ethyl, propyl, hexyl, octyl, 2-ethylhexyl, decyl, dodecyl, tetradecyl, hexadecyl and octadecyl; alkenyl groups (preferably C2-40 and more preferably C2-20 alkenyl groups) such as vinyl, 2-buten-1-yl and oleyl), alkynyl groups (preferably $C_{2-40}$ and more preferably $C_{2-20}$ alkynyl groups) such as propargyl; aryl groups (preferably $C_{6-40}$ and more preferably $C_{6-20}$ aryl groups) such as phenyl and naphthyl), heterocyclic groups (preferably $C_{1-40}$ and more preferably $C_{1-20}$ heterocyclic groups) such as 2-furyl, 2-thyenyl, 4-pyridyl, 2-imidazolyl, 2-benzothiazolyl, 2-benzooxazolyl and 1-benzoimidazolyl; cyano; hydroxyl; nitro; carboxyl; alkoxy groups (preferably $C_{1-40}$ and more preferably $C_{1-20}$ alkoxy groups) such as methoxy, ethoxy, hexyloxy, octyloxy, 2-ethylhexyloxy, decyloxy, dodecyloxy, tetradecyloxy, hexadecyloxy and octadecyloxy; aryloxy groups (preferably $C_{6-40}$ and more preferably $C_{6-20}$ aryloxy groups) such as phenoxy and 1-naphthoxy; silyloxy groups (preferably $C_{3-40}$ and more preferably $C_{3-20}$ silyloxy group) such as trimethyl silyloxy; heteroxy groups (preferably $C_{1-40}$ and more preferably $C_{1-20}$ heteroxy groups) such as 2-furyloxy, 2-tetrahydropyranyloxy, 3-pylidyloxy and 2-imidazolyloxy; acyloxy groups (preferably $C_{2-40}$ and more preferably $C_{2-20}$ acyloxy groups) such as acetoxy, butanoyloxy, octanoyloxy, dodecanoyloxy and benzoyloxy; carbamoyloxy groups (preferably $C_{1-40}$ and more preferably $C_{1-20}$ carbamoyloxy groups) such as N,N-diethyl carbamoyloxy; alkoxycarbonyloxy groups (preferably $C_{2-40}$ and more preferably $C_{2-20}$ alkoxycarbonyloxy groups) such as ethoxycarbonyloxy, butoxycarbonyloxy, 2-ethylhexyloxycarbonyloxy, dodecyloxycarbonyloxy, and hexadecyloxycarbonyloxy; aryloxycarbonyloxy groups (preferably $C_{7-40}$ and more preferably $C_{7-20}$ aryloxycarbonyloxy groups) such as phenoxycarbonyloxy; amino groups (preferably $C_{0-40}$ and more preferably $C_{1-20}$ amino groups) such as amino, N-methylamino, N-2-ethylhexylamino, N-tetradecylamino, N,N-diethylamino and N,N-dioctylamino; acylamino groups (preferably $C_{1-40}$ and more preferably $C_{1-20}$ acyl amino groups) such as acetylamino, octanoylamino and dodecanoylamino; aminocarbonylamino groups (preferably $C_{1-40}$ and more preferably $C_{1-20}$ aminocarbonylaminogroups) such as N,N-dioctyl carbamoylamino; alkoxycarbonylamino groups (preferably $C_{2-40}$ and more preferably $C_{2-20}$ alkoxycarbonylamino groups) such as methoxycarbonylamino, ethoxycarbonylamino, 2-ethylhexylcarbonylamino and tetradecyloxycarbonylamino; aryloxycarbonylamino groups (preferably $C_{7-40}$ and more preferably $C_{7-20}$ aryloxycarbonylamino groups) such as phenoxycarbonylamino; sulfamoylamino groups (preferably $C_{0-40}$ and more preferably $C_{0-20}$ sulfamoylamino groups) such as N,N-dimethylsulfamoylamino; alkyl- and aryl-sulfonylamino groups (preferably $C_{1-40}$ and more preferably $C_{1-20}$ alkyl- and aryl-sulfonylamino groups) such as methyl sulfonylamino, butyl sulfonylamino, dodecyl sulfonylamino and p-toluene sulfonylamino; mercapto; alkylthio groups (preferably $C_{1-40}$ and more preferably $C_{1-20}$ alkylthio groups) such as methylthio, ethylthio, 2-ethylthio and dodecylthio; arylthio groups (preferably $C_{6-40}$ and more preferably $C_{6-20}$ arylthio groups) such as phenylthio; heterocyclic-thio groups (preferably $C_{1-40}$ and more preferably $C_{1-20}$ heterocyclic-thio groups) such as 4-pylidylthio, thiazole-2-ylthio, benzoxazole-2-ylthio, 1-phenyltetrazole-5-ylthio and 1,3,4-thiadiazole-2-ylthio; sulfamoyl groups (preferably C0-40 and more preferably C0-20 sulfamoyl groups) such as sulfamoyl, N,N-diethyl sulfamoyl and N-hexadecyl sulfamoyl; sulfo; alkyl- and aryl-sulfinyl groups (preferably $C_{1-40}$ and more preferably $C_{1-20}$ alkyl- and aryl-sulfinyl groups) such as methyl sulfinyl and phenyl sulfinyl; alkyl- and aryl-sulfonyl groups (preferably $C_{1-40}$ and more preferably $C_{1-20}$ alkyl- and aryl-sulfonyl groups) such as methyl sulfonyl, butyl sulfonyl, hexadecyl sulfonyl and p-tolyl sulfonyl; acyl groups (preferably $C_{1-40}$ and more preferably $C_{1-20}$ acyl groups) such as acetyl, propionyl, isobutyl, tetradecanoyl and benzoyl; aryloxy carbonyl groups (preferably $C_{7-40}$ and more preferably $C_{7-20}$ aryloxy carbonyl groups) such as phenoxycarbonyl; alkoxycarbonyl groups (preferably $C_{2-40}$ and more preferably $C_{2-20}$ alkoxycarbonyl groups) such as ethoxycarbonyl, t-butoxycarbonyl and hexadecylcarbonyl; carbamoyl groups (preferably $C_{1-40}$ and more preferably $C_{1-20}$ carbamoyl groups) such as carbamoyl, N,N-diethyl carbamoyl and N-dodecyl carbamoyl; aryl- and heterocyclic-azo groups (preferably C1-40 and more preferably C1-20 aryl- and heterocyclic-azo groups) such as phenylazo, 3-methyl-1,2,4-oxadiazole-5-ylazo, and 2-methylthio-1,3,4-thiadiazole-5-ylazo; imido groups (preferably $C_{4-40}$ and more preferably $C_{4-20}$ imido groups) such as succinimido and phthalimido; phosphino groups (preferably $C_{0-40}$ and more preferably $C_{0-20}$ phosphino groups); phosphinyl groups (preferably $C_{0-40}$ and more preferably $C_{0-20}$ phosphinyl groups); phosphinyloxy groups (preferably $C_{0-40}$ and more preferably $C_{0-20}$ phosphinyloxy groups); phosphinylamino groups (preferably $C_{0-40}$ and more preferably $C_{0-20}$ phosphinylamino groups); and silyl groups (preferably $C_{3-40}$ and more preferably $C_{3-20}$ silyl groups) such as trimethyl silyl and t-butyldimethyl silyl. Examples of substituent $R^{71}$ or $R^{72}$ also include these substituents having at least one selected from these substituents.

Preferably, substituent $R^{71}$ is an alkoxy, alkoxycarbonyl or acyl group having a linear or branched alkyl residue therein.

In the formula, "a" is an integer from 0 to 5, and preferably from 1 to 3.

The number of carbon atoms in $R^{71}$ is preferably from 1 to 40, and more preferably from 1 to 20.

The compound represented by formula (1), in which "D" is a heterocyclic core such as 1,3,5-triazine core, that is, a cyclic group represented by [2], having at least one hetero atom such as a nitrogen and oxygen atom, preferably has at least one groups represented by formula (8) shown below as one of three "—X—R" groups.

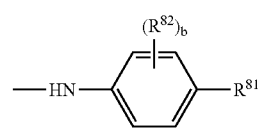

(8)

In the formula, $R^{81}$ and $R^{82}$ each represent a substituent, and examples of the substituent are same as those exemplified as substituent represented by $R^{25}$. Preferably, $R^{81}$ and $R^{82}$ each is a substituent represented by any one of formulae (4), (4a), (4b), (5), (6) and (7), and more preferably by formula (4) or (5).

In the formula, b is an integer from 0 to 4 and preferably 0 or 1.

On the other hand, the compound represented by formula (1), in which "D" is a hydrocarbon-cyclic core such as benzene ring core or triphenylene ring core, that is, a cyclic group represented by [1] or [3], having no hetero atom such as a nitrogen and oxygen atom, preferably has at least one groups represented by any one of formulae (4), (4a), (4b), (5), (6) and (7), more preferably by any one of formulae (4), (5), (6) and (7), and even more preferably formula (4) or (6), as one of three "—X—R" groups.

Examples of the compound represented by formula (1) employable in the invention include those described in JPA No. 2006-257384, paragraphs from [0056] to [0085].

And preferable examples of the compound represented by formula (1) employable in the invention include the compounds represented by formula (a1), (a2) and (a3) shown below.

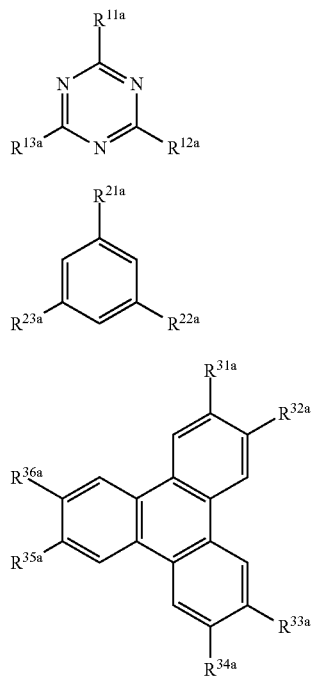

In the formulae, $R^{11a}$, $R^{12a}$, $R^{13a}$, $R^{21a}$, $R^{22a}$, $R^{23a}$, $R^{31a}$, $R^{32a}$, $R^{33a}$, $R^{34a}$, $R^{35a}$ and $R^{36a}$ each represent a group denoted by any one of formulae (4) to (7). Preferably, all of $R^{11a}$, $R^{12a}$ and $R^{13a}$ each represent a group denoted by formula (7), or two of them each represent a group denoted by formula (7) and one of them is a group denoted by formula (5). Preferably, all of $R^{21a}$, $R^{22a}$ and $R^{23a}$ each represent a group denoted by formula (4). Preferably, all of $R^{31a}$, $R^{32a}$, $R^{33a}$, $R^{34a}$, $R^{35a}$ and $R^{36a}$ each represent a group denoted by formula (6).

Ingredient (a)

Ingredient (b) consists of one or more selected from the compounds represented by formula (2).

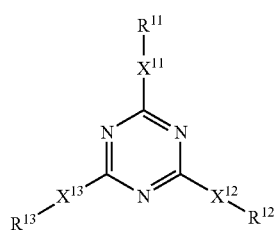

In the formula, $X^{11}$, $X^{12}$ and $X^{13}$ each independently represent a single bond or a bivalent linking group selected from the group consisting of $NR^a$ (where $R^a$ is a hydrogen atom or a $C_{1-30}$ alkyl group), an oxygen atom, a sulfur atom, carbonyl, sulfonyl and any combinations thereof, provided that at least one of $X^{11}$, $X^{12}$ and $X^{13}$ represents $NR^b$ (where $R^b$ represents a $C_{1-30}$ alkyl group).

In the case that each of $X^{11}$, $X^{12}$ and $X^{13}$ is a single bond, it may bind directly to nitrogen atom, having free atomic valence, of a heterocyclic group such as a piperidine residue, or may bind to a heteroatom not having free atomic valence to form an onium salt such as an oxonium salt, sulfonium salt or ammonium salt.

In the case that each of $X^{11}$, $X^{12}$ and $X^{13}$ is not a single bond, $X^{11}$, $X^{12}$ and $X^{13}$ each independently represent a bivalent linking group selected from the group consisting of $NR^a$ (where $R^a$ is a hydrogen atom or a $C_{1-30}$ alkyl group), an oxygen atom, a sulfur atom, carbonyl, sulfonyl and any combinations thereof. Examples of the bivalent linking group include oxycarbonyl, aminocarbonyl, ureylene, oxysulfonyl and sulfamoyl. Preferred are sulfur atom and $NR^a$, where $R^a$ preferably represents a $C_{1-30}$ alkyl group and more preferably $C_3$ or shorter alkyl group such as methyl, ethyl, n-propyl and iso-propyl.

At least one of $X^{11}$, $X^{12}$ and $X^{13}$ is $NR^b$, where $R^b$ is an alkyl group. Preferably, $R^b$ is a $C_{1-30}$ alkyl group, more preferably $C_3$ or shorter alkyl group such as methyl, ethyl, n-propyl and iso-propyl, and most preferably methyl. Preferably, two of $X^{11}$, $X^{12}$ and $X^{13}$ are groups of $NR^b$.

In formula (2), $R^{11}$, $R^{12}$ and $R^{13}$ each independently a substituted or non-substituted alkyl group, alkenyl group, alkynyl group, aryl group or heterocyclic group.

Preferably, $R^{11}$, $R^{12}$ and $R^{13}$ each represent a $C_{1-40}$, more preferably from $C_{2-30}$, much more preferably from $C_{4-30}$ alkyl groups and even much more preferably from $C_{6-30}$ alkyl groups. The alkyl group may have a linear or branched chain structure. And the alkyl group may have one or more substituents. Examples of the substituent include halogen atoms, $C_{1-40}$, preferably $C_{1-20}$, alkoxy groups such as methoxy, ethoxy, methoxyethoxy and phenoxy; $C_{1-40}$, preferably $C_{1-20}$, alkylthio groups and $C_{6-40}$, preferably $C_{6-20}$, arylthio groups such as methylthio, ethylthio, propylthio and phenylthio; $C_{1-40}$, preferably $C_{1-20}$, alkylamino groups such as methylamino and propylamino; $C_{1-40}$, preferably $C_{1-20}$, acyl groups such as acetyl, propanoyl, octanoyl and benzoyl; $C_{1-40}$, preferably $C_{2-20}$, acyloxy groups such as acetoxy, pivaloyloxy and benzoyloxy; hydroxyl, mercapto, amino, carboxyl, sulfo, carbamoyl, sulfamoyl and ureido.

The alkenyl or alkynyl group represented by $R^{11}$, $R^{12}$ or $R^{13}$ is preferably selected from $C_{2-40}$ alkenyl or alkynyl groups, more preferably selected from $C_{2-30}$ alkenyl or alkynyl groups, much more preferably selected from $C_{4-30}$ alkenyl or alkynyl groups and even much more preferably selected from $C_{6-30}$ alkenyl or alkynyl groups. The alkenyl or alkynyl group may have a linear or branched chain structure. The alkenyl or alkynyl group may have one or more substituents selected from the groups exemplified above as substituents of the alkyl group.

Examples of the aryl group represented by $R^{11}$, $R^{12}$ or $R^{13}$ include phenyl, indenyl, alpha-naphthyl, beta-naphthyl, fluorenyl, phenanthryl, anthracenyl and pyrenyl. Among these, more preferred are phenyl and naphthyl. The aryl group may have one or more substituents. Examples of the substituent include $C_{1-40}$ alkyl groups and those exemplified above as substituents of the alkyl group. It is preferred that the aryl group has one or more substituents containing a $C_{8-30}$ linear or branched alkyl residue, such as alkyl groups (e.g. octyl, decyl, hexadecyl and 2-ethylhexyl); alkoxy groups (e.g. dodecyloxy, hexadecyloxy and 2-hexyldecyloxy, and hexyloxy ethyleneoxy ethyleneoxy); sulfide groups (e.g. hexadecylthio); substituted amino groups (e.g. heptadecyl amino), octyl carbamoyl, octanoyl and decyl sulfamoyl. The aryl group preferably has two or more substituents selected from the substituents containing a $C_{8-30}$ linear or branched alkyl residue. The aryl group may have one or more substituents selected from other substituents such as halogen atoms, hydroxyl, cyano, nitro, carboxyl and sulfo.

The heterocyclic group represented by $R^{11}$, $R^{12}$ or $R^{13}$ is preferably selected from 5-, 6- or 7-membered heterocyclic groups, more preferably selected from 5- or 6-membered heterocyclic groups, and much more preferably selected from 6-membered heterocyclic groups. The heterocyclic group may contain a single ring or a condensed ring formed of two or more rings. Specific examples of such skeletons can be found in hetero rings listed in "Iwanami Rikagaku Jiten (Iwanami's Physicochemical Dictionary; Iwanami Shoten, Publishers), the 3rd edition, supplement Chapter 11 "Nomenclature for Organic Chemistry", Table 4 "Names of Principal Hetero Monocyclic Compounds" on page 1606, and Table 5 "Names of Principal Condensed Heterocyclic Compounds" on page 1607. The heterocyclic groups are, similarly to the foregoing aryl group, preferably substituted with a substituent containing a $C_8$ or longer linear or branched alkyl chain, where substitution by two or more groups is more preferable. Specific examples of the substituent including such chain are same as those described in the above. The heterocyclic group may also be substituted by halogen atom, hydroxyl, cyano, nitro, carboxyl, sulfo or the like, besides the foregoing substituents.

Preferably, at least one of $R^{11}$, $R^{12}$ and $R^{13}$ contains one or more ester bonds; and more preferably, at least one of $R^{11}$, $R^{12}$ and $R^{13}$ is an alkoxy group having one or more substituents containing a linear or branched alkyl residue containing one or more ester bonds. Much more preferably, all of $R^{11}$, $R^{12}$ and $R^{13}$ contain one or more ester bonds; and even much more preferably, all of $R^{11}$, $R^{12}$ and $R^{13}$ are alkoxy groups having one or more substituents containing a linear or branched alkyl residue containing one or more ester bonds.

Preferably, $R^{11}$, $R^{12}$ and $R^{13}$ each contain at least one linear or branched alkyl chain having the total number of carbon atoms equal to or greater than 8, linear or branched oligoalkyleneoxy chain having the total number of the carbon atoms equal to or greater than 4, linear or branched perfluoroalkyl chain having the total number of carbon atoms equal to or greater than 2, or linear or branched perfluoroalkylether chain having the total number of carbon atoms equal to or greater than 2, or linear or branched organic polysiloxyl chain. And more preferably, $R^{11}$, $R^{12}$ and $R^{13}$ each represent a phenyl group having one or more substituents containing at least one linear or branched oligoalkyleneoxy chain having the total number of the carbon atoms equal to or greater than 4.

In formula (2), preferably, at least one of $R^{11}$—$X^{11}$, $R^{12}$—$X^{12}$ and $R^{13}$—$X^{13}$ is a group represented by formula (3).

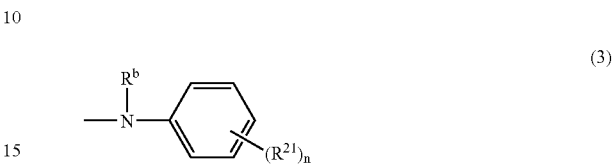

(3)

In the formula, $R^b$ represents a $C_{1-30}$ alkyl group, preferably represents a $C_3$ or shorter alkyl group, and most preferably represents methyl.

In the formula, $R^{21}$ represents a substituted or non-substituted alkyl group, alkenyl group, alkynyl group, aryl group or heterocyclic group. Preferably, $R^{21}$ contains a linear or branched alkyl chain having the total number of carbon atoms equal to or greater than 8, linear or branched oligoalkyleneoxy chain having the total number of the carbon atoms equal to or greater than 4, linear or branched perfluoroalkyl chain having the total number of carbon atoms equal to or greater than 2, or linear or branched perfluoroalkylether chain having the total number of carbon atoms equal to or greater than 2, or linear or branched organic polysiloxyl chain. And more preferably, $R^{21}$ represents a substituent containing at least one linear or branched alkyl chain having the total number of carbon atoms equal to or greater than 8, or at least one linear or branched oligoalkyleneoxy chain having the total number of the carbon atoms equal to or greater than 4; and even more preferably, a substituent containing at least one linear or branched oligoalkyleneoxy chain having the total number of the carbon atoms equal to or greater than 4. More specifically, preferably, $R^{21}$ is a group of —$O(C_nH_{2n}O)_l C_mH_{2m+1}$ where l is an integer from 1 to 10, n is an integer from 2 to 6, and m is an integer from 1 to 24.

In the formula, n is an integer from 1 to 5.

Examples of the compound represented by formula (2) employable in the invention include, but are not limited to, those shown below.

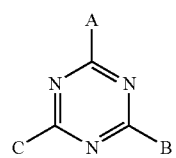

| | A = B | C |
|---|---|---|
| b-1 | 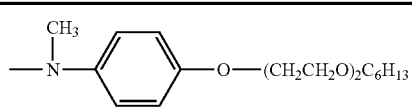 | —$OC_6H_{13}$ |
| b-2 | 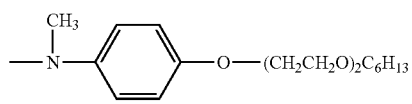 | —$OC_{12}H_{25}$ |

-continued

| | | |
|---|---|---|
| b-3 | CH₃−N(CH₃)−C₆H₄−O−(CH₂CH₂O)₂C₆H₁₃ | −O−CH₂−CH(C₂H₅)−C₄H₉ |
| b-4 | CH₃−N(CH₃)−C₆H₄−O−(CH₂CH₂O)₂C₆H₁₃ | −O−(CH₂CH₂O)₂C₆H₁₃ |
| b-5 | CH₃−N(CH₃)−C₆H₄−O−(CH₂CH₂O)₂C₆H₁₃ | −O−(CH₂CH₂O)₂−CH₂−CH(C₂H₅)−C₄H₉ |
| b-6 | CH₃−N(CH₃)−C₆H₄−O−(CH₂CH₂O)₂C₆H₁₃ | −O−(CH₂CH₂O)₃CH₃ |
| b-7 | CH₃−N(CH₃)−C₆H₄−O−(CH₂CH₂O)₂C₆H₁₃ | −O−(CH₂CH₂O)₄C₄H₉ |
| b-8 | CH₃−N(CH₃)−C₆H₄−O−(CH₂CH₂O)₂C₆H₁₃ | −O−(CH₂CH₂O)₄−CH₂−CH(C₂H₅)−C₄H₉ |
| b-9 | CH₃−N(CH₃)−C₆H₄−O−(CH₂CH₂O)₂C₆H₁₃ | −O−CH₂FCF₂(OCF₂CF₂)₂OC₃F₇ |
| b-10 | CH₃−N(CH₃)−C₆H₄−O−(CH₂CH₂O)₂C₆H₁₃ | −O−CH₂(OCF₂)₂(OCF₂CF₂)₂CF₃ |
| b-11 | CH₃−N(CH₃)−C₆H₄−O−(CH₂CH₂O)₂C₆H₁₃ | −N(C₄H₉)(C₄H₉) |
| b-12 | CH₃−N(CH₃)−C₆H₄−O−(CH₂CH₂O)₂C₆H₁₃ | −N(C₈H₁₇)(C₈H₁₇) |
| b-13 | CH₃−N(CH₃)−C₆H₄−O−(CH₂CH₂O)₂C₆H₁₃ | −N(CH₂CH(C₂H₅)C₄H₉)(CH₂CH(C₂H₅)C₄H₉) |
| b-14 | CH₃−N(CH₃)−C₆H₄−O−(CH₂CH₂O)₂C₆H₁₃ | −N(C₁₂H₂₅)(C₁₂H₂₅) |
| b-15 | CH₃−N(CH₃)−C₆H₄−O−(CH₂CH₂O)₂C₆H₁₃ | −NH−C₁₂H₂₅ |
| b-16 | CH₃−N(CH₃)−C₆H₄−O−(CH₂CH₂O)₂C₆H₁₃ | −N(CH₂CO₂C₂H₅)(CH₂CO₂C₂H₅) |

-continued
| | | |
|---|---|---|
| b-17 | 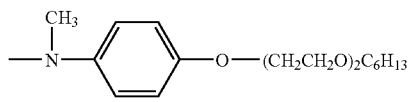 | 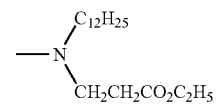 |
| b-18 | 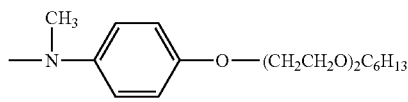 | 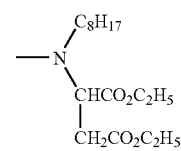 |
| b-19 | 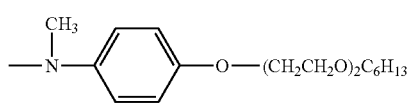 | 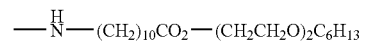 |
| b-20 | 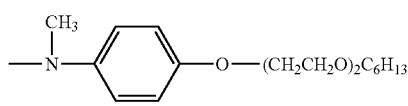 | 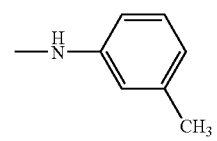 |
| b-21 | 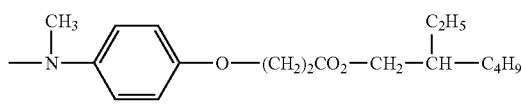 | 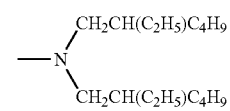 |
| b-22 | 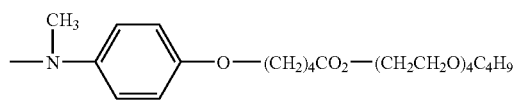 | 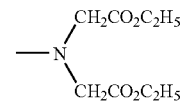 |
| b-23 | 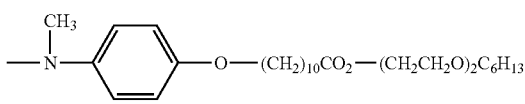 | 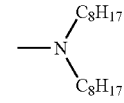 |
| b-24 | 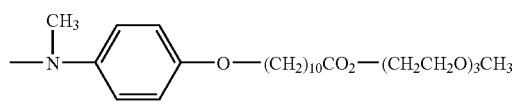 | 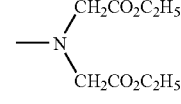 |
| b-25 | 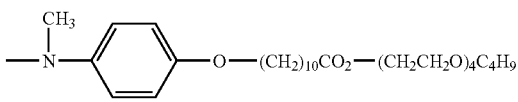 | 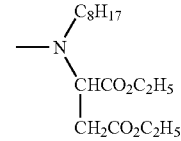 |
| b-26 | 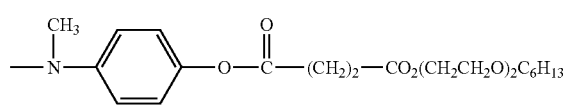 | 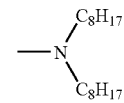 |
| b-27 | 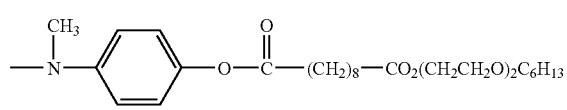 | 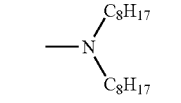 |
| b-28 | 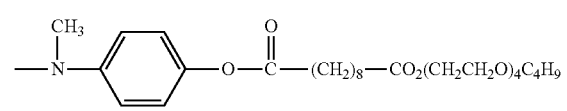 | 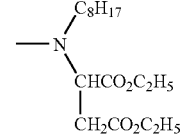 |

| | | |
|---|---|---|
| b-29 | 3-(N,N-dimethylamino)phenyl-O-(CH$_2$)$_2$CO$_2$-CH$_2$-CH(C$_2$H$_5$)-C$_4$H$_9$ | $-$NH$-$(CH$_2$)$_{10}$CO$_2-$(CH$_2$CH$_2$O)$_2$C$_6$H$_{13}$ |
| b-30 | 3-(N,N-dimethylamino)phenyl-O-C(=O)-(CH$_2$)$_2$-CO$_2$(CH$_2$CH$_2$O)$_2$C$_6$H$_{13}$ | $-$N(C$_{12}$H$_{25}$)$-$CH$_2$CH$_2$CO$_2$C$_2$H$_5$ |
| b-31 | 4-(N,N-dimethylamino)phenyl-O-(CH$_2$)$_2$CO$_2$-CH$_2$-CH(C$_2$H$_5$)-C$_4$H$_9$ | $-$O$-$(CH$_2$CH$_2$O)$_4$C$_4$H$_9$ |
| b-32 | 4-(N,N-dimethylamino)phenyl-O-(CH$_2$)$_4$CO$_2$-(CH$_2$CH$_2$O)$_4$C$_4$H$_9$ | $-$O$-$(CH$_2$CH$_2$O)$_4$C$_4$H$_9$ |
| b-33 | 4-(N,N-dimethylamino)phenyl-O-(CH$_2$)$_{10}$CO$_2$-(CH$_2$CH$_2$O)$_2$C$_6$H$_{13}$ | $-$O$-$(CH$_2$CH$_2$O)$_4$C$_4$H$_9$ |
| b-34 | 4-(N,N-dimethylamino)phenyl-O-(CH$_2$)$_{10}$CO$_2$-(CH$_2$CH$_2$O)$_3$CH$_3$ | $-$O$-$(CH$_2$CH$_2$O)$_4$C$_4$H$_9$ |
| b-35 | 4-(N,N-dimethylamino)phenyl-O-(CH$_2$)$_{10}$CO$_2$-(CH$_2$CH$_2$O)$_4$C$_4$H$_9$ | $-$O$-$(CH$_2$CH$_2$O)$_4$C$_4$H$_9$ |
| b-36 | 4-(N,N-dimethylamino)phenyl-O-C(=O)-(CH$_2$)$_2$-CO$_2$(CH$_2$CH$_2$O)$_2$C$_6$H$_{13}$ | $-$O$-$(CH$_2$CH$_2$O)$_2$C$_6$H$_{13}$ |
| b-37 | 4-(N,N-dimethylamino)phenyl-O-C(=O)-(CH$_2$)$_8$-CO$_2$(CH$_2$CH$_2$O)$_2$C$_6$H$_{13}$ | $-$O$-$(CH$_2$CH$_2$O)$_2$C$_6$H$_{13}$ |
| b-38 | 4-(N,N-dimethylamino)phenyl-O-C(=O)-C$_6$H$_4$-O(CH$_2$CH$_2$O)$_4$C$_4$H$_9$ | $-$O$-$(CH$_2$CH$_2$O)$_2$C$_6$H$_{13}$ |
| b-39 | 3-(N,N-dimethylamino)phenyl-O-(CH$_2$)$_2$CO$_2$-CH$_2$-CH(C$_2$H$_5$)-C$_4$H$_9$ | $-$O$-$(CH$_2$CH$_2$O)$_2$C$_6$H$_{13}$ |
| b-40 | 3-(N,N-dimethylamino)phenyl-O-C(=O)-(CH$_2$)$_2$-CO$_2$(CH$_2$CH$_2$CH$_2$O)$_2$C$_6$H$_{13}$ | $-$O$-$(CH$_2$CH$_2$O)$_2$C$_6$H$_{13}$ |

-continued
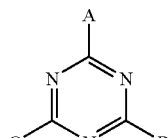
A = B = C
b-41 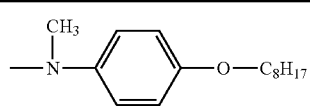
b-42 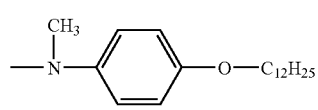
b-43 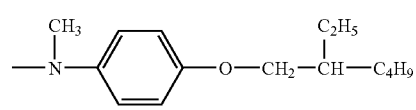
b-44 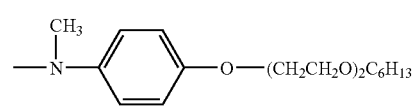
b-45 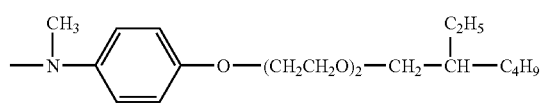
b-46 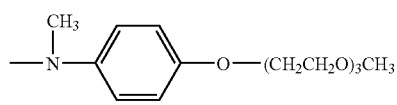
b-47 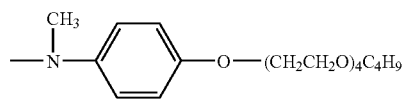
b-48 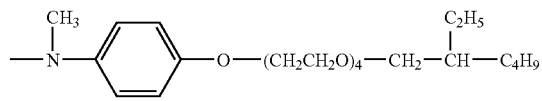
b-49 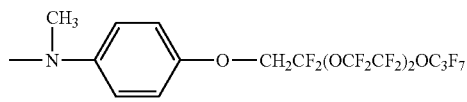
b-50 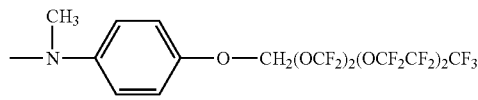
b-51 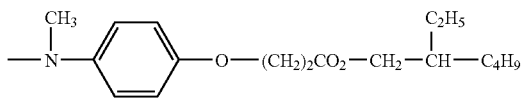
b-52 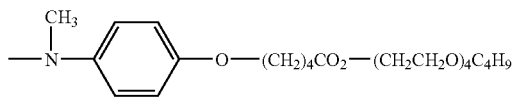

-continued
b-53 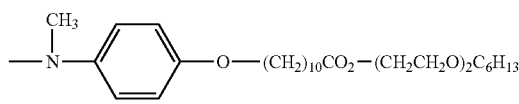
b-54 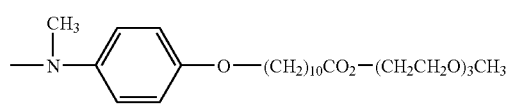
b-55 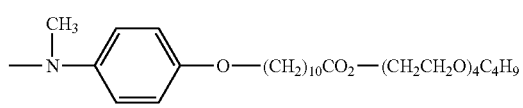
b-56 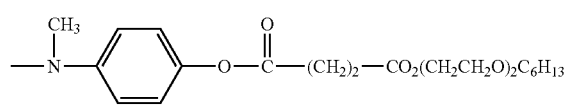
b-57 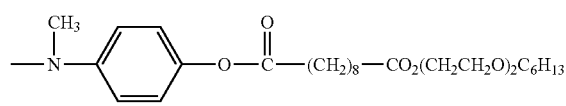
b-58 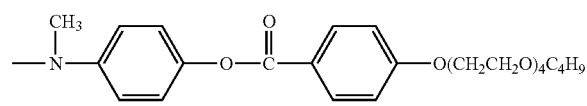
b-59 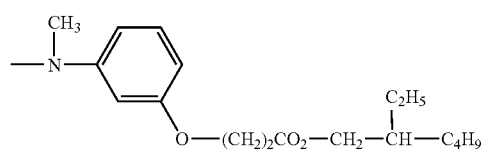
b-60 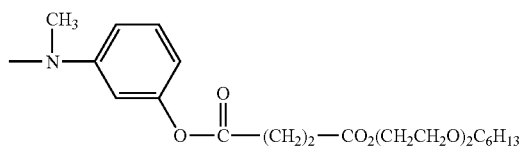
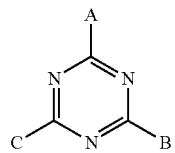
| | A | B | C |
|---|---|---|---|
| b-61 | 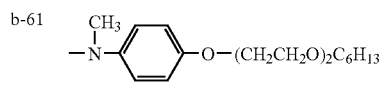 | 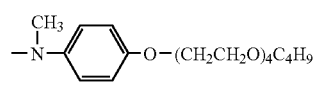 | 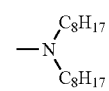 |
| b-62 | 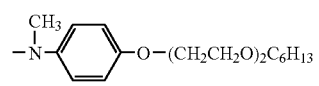 | 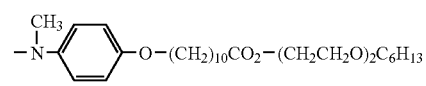 |  |
| b-63 | 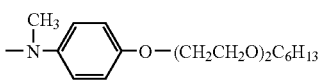 | 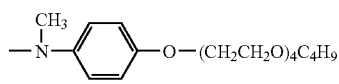 | 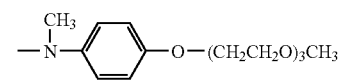 |
| b-64 | 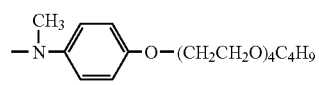 | 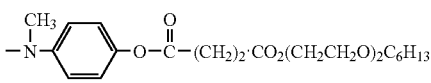 | 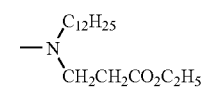 |

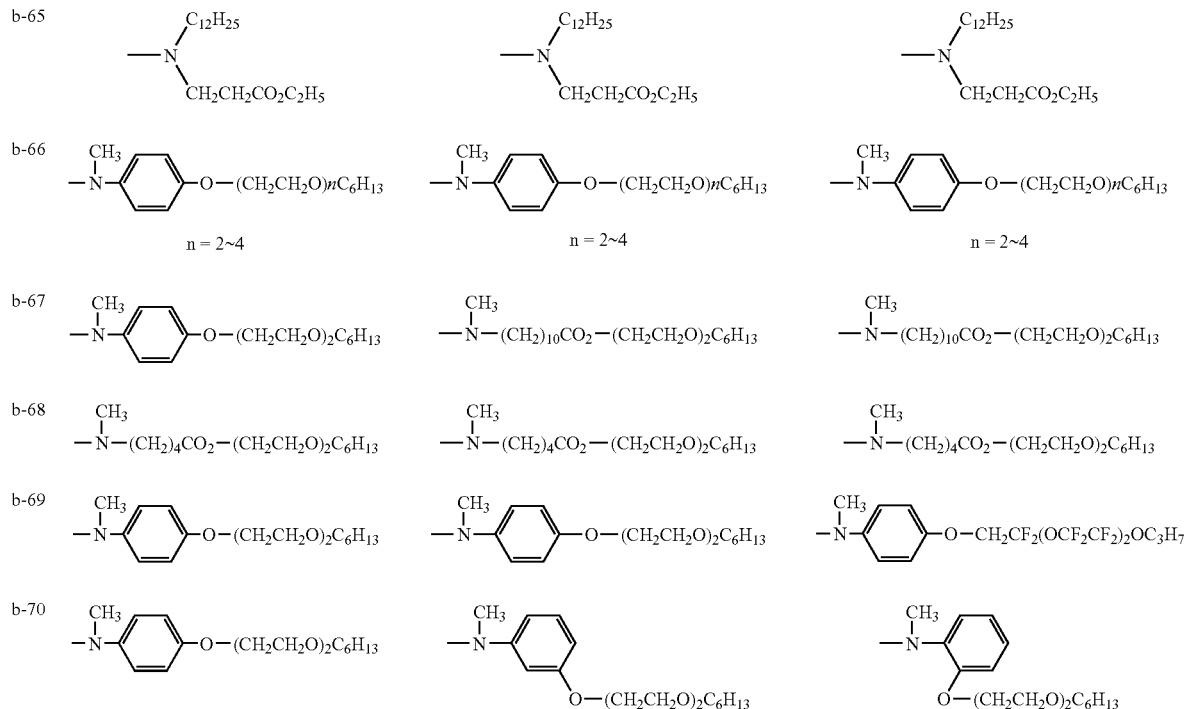
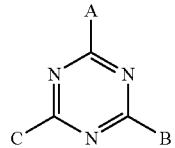
A = B = C
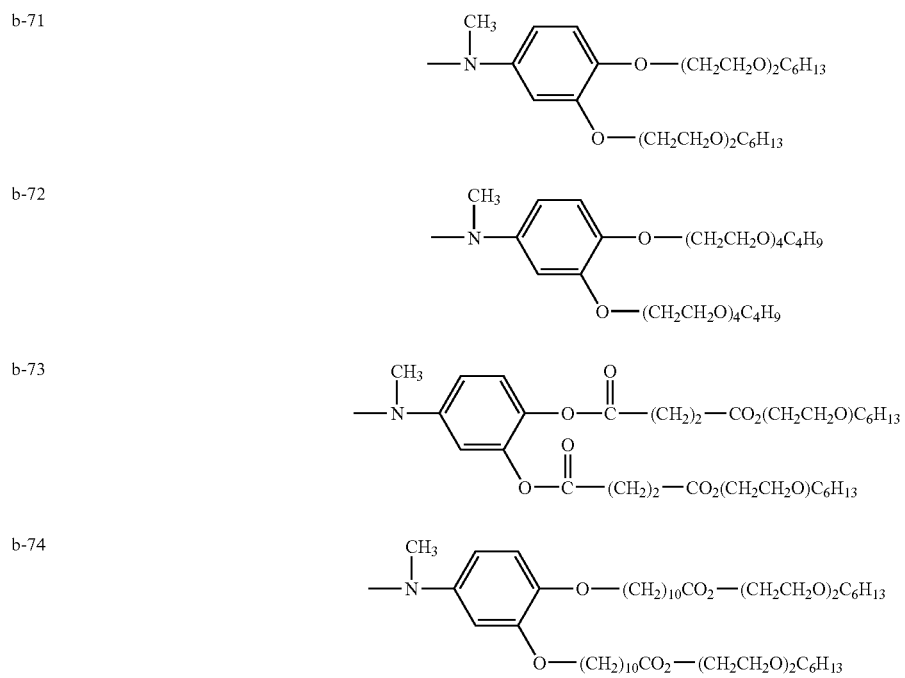

-continued
b-75 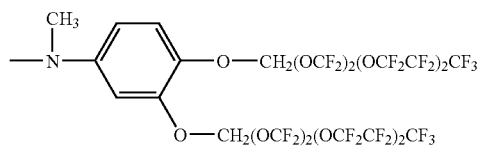
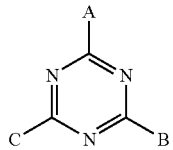
| | A = B | C |
|---|---|---|
| b-76 | 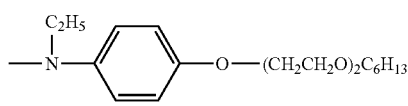 | 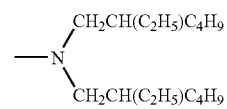 |
| b-77 | 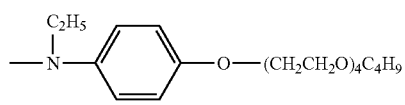 | 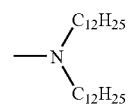 |
| b-78 | 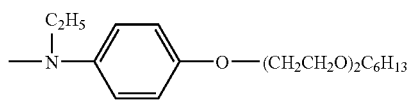 | 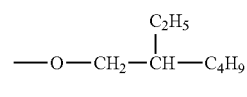 |
| b-79 | 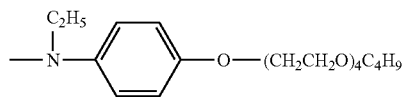 |  |
| b-80 | 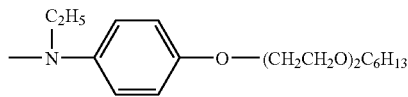 | 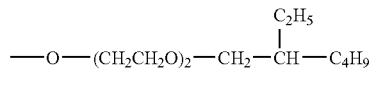 |
| b-81 | 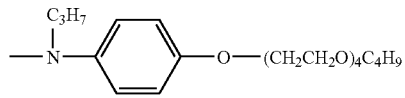 | 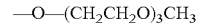 |
| b-82 | 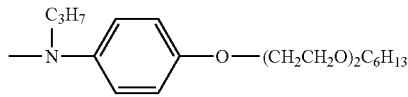 | 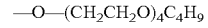 |
| b-83 | 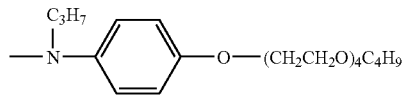 | 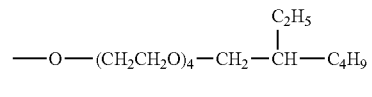 |
| b-84 | 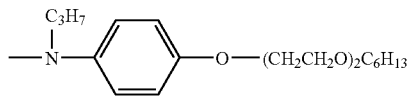 | 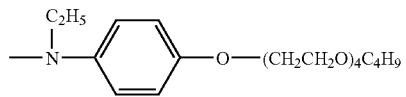 |
| b-85 | 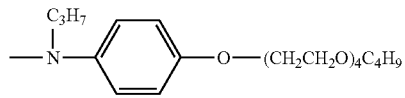 | 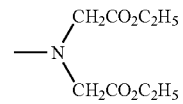 |

-continued
| | | |
|---|---|---|
| b-86 | 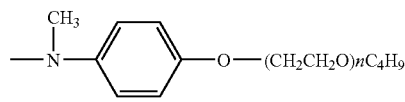<br>n ≒ 2 (n: average number) | —OC₆H₁₃ |
| b-87 | 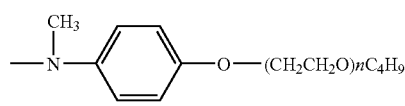<br>n ≒ 2 (n: average number) | —OC₁₂H₂₅ |
| b-88 | 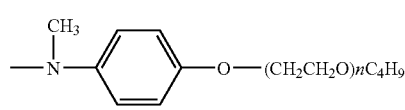<br>n ≒ 2 (n: average number) | 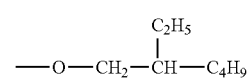 |
| b-89 | 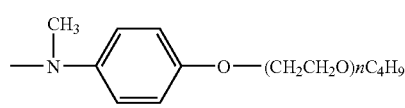<br>n ≒ 4 (n: average number) | —O—(CH₂CH₂O)₂C₆H₁₃ |
| b-90 | 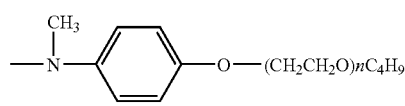<br>n ≒ 4 (n: average number) | 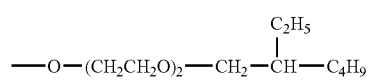 |
| b-91 | 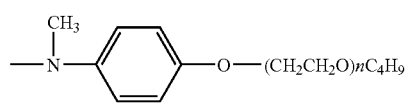<br>n ≒ 4 (n: average number) | —O—(CH₂CH₂O)₃CH₃ |
| b-92 | 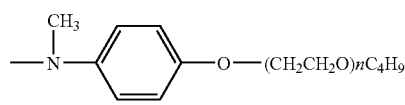<br>n ≒ 4 (n: average number) | —O—(CH₂CH₂O)₄C₄H₉ |
| b-93 | 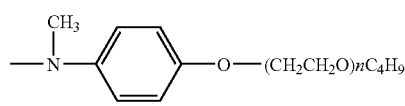<br>n ≒ 6 (n: average number) | —O—(CH₂CH₂O)₄C₄H₉ |
| b-94 | 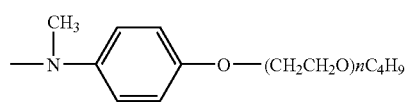<br>n ≒ 10 (n: average number) | —O—(CH₂CH₂O)₄C₄H₉ |

-continued
b-95 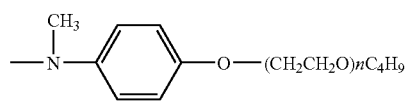
n ≒ 4 (n: average number)
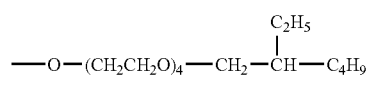
b-96 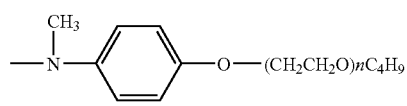
n ≒ 2 (n: average number)
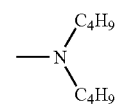
b-97 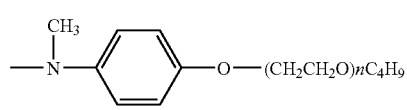
n ≒ 4 (n: average number)
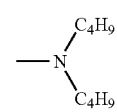
b-98 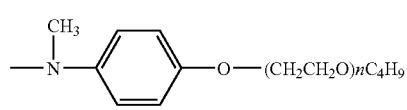
n ≒ 6 (n: average number)
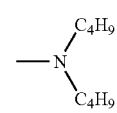
b-99 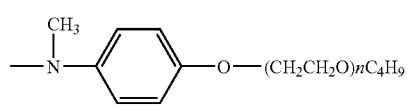
n ≒ 10 (n: average number)
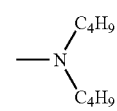
b-100 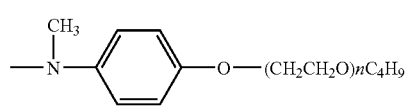
n ≒ 4 (n: average number)
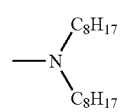
b-101 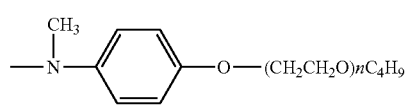
n ≒ 6 (n: average number)
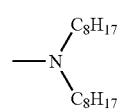
b-102 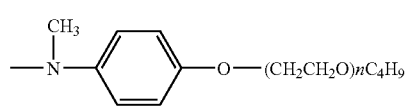
n ≒ 4 (n: average number)
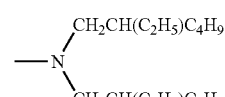
b-103 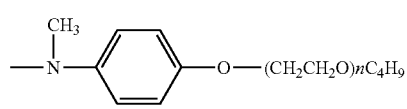
n ≒ 6 (n: average number)
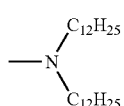

| | | |
|---|---|---|
| b-104 | 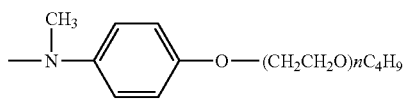 n ≒ 2 (n: average number) | 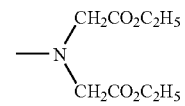 |
| b-105 | 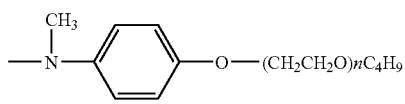 n ≒ 4 (n: average number) | 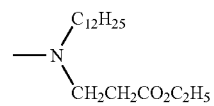 |
| b-106 | 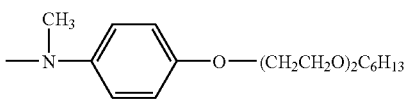 |  —O—(CH$_2$CH$_2$O)$_2$C$_6$H$_{13}$ |
| b-107 | 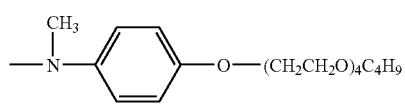 | 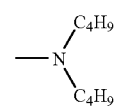 |
| b-108 | 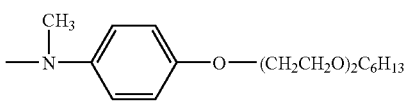 | 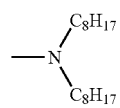 |
| b-109 | 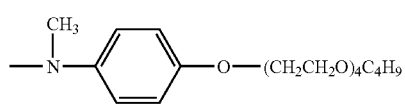 | 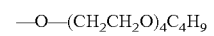 —O—(CH$_2$CH$_2$O)$_4$C$_4$H$_9$ |
| b-110 | 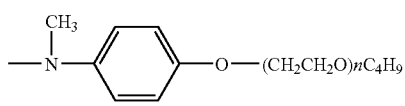 n ≒ 2 (n: average number) | 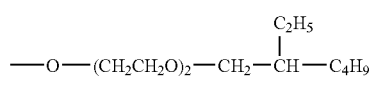 |
| b-111 | 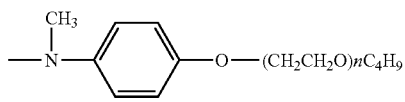 n ≒ 4 (n: average number) | 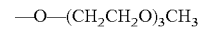 —O—(CH$_2$CH$_2$O)$_3$CH$_3$ |
| b-112 | 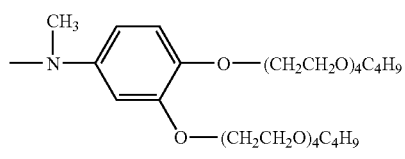 |  —O—(CH$_2$CH$_2$O)$_4$C$_4$H$_9$ |
| b-113 | 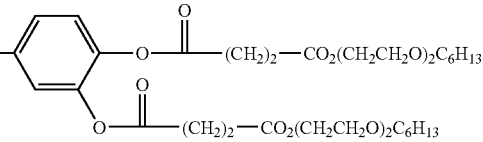 | 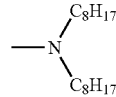 |
| b-114 | 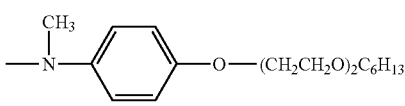 | 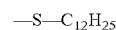 —S—C$_{12}$H$_{25}$ |

| | | |
|---|---|---|
| b-115 | CH₃–N–C₆H₄–O–(CH₂CH₂O)₂C₆H₁₃ | —O—CH₂(OCF₂)₂(OCF₂CF₂)₂CF₃ |
| b-116 | CH₃–N–C₆H₄–O(CH₂CH₂O)₄C₄H₉ | —N(C₄H₉)₂ |
| b-117 | CH₃–N–C₆H₄–O(CH₂CH₂O)₄C₄H₉ | —N(C₈H₁₇)₂ |
| b-118 | CH₃–N–C₆H₄–O(CH₂CH₂O)₄C₄H₉ | —N(C₄H₉)₂ |
| b-119 | CH₃–N–C₆H₄–O(CH₂CH₂O)₄C₄H₉ | —N(CH₂CH(C₂H₅)C₄H₉)₂ |
| b-120 | CH₃–N–C₆H₄–O(CH₂CH₂O)₆C₄H₉ | —N(C₄H₉)₂ |
| b-121 | CH₃–N–C₆H₄–O(CH₂CH₂O)₂CH₂CH(C₂H₅)C₄H₉ | —N(C₄H₉)₂ |
| b-122 | CH₃–N–C₆H₄–O—(CH₂CH₂O)nC₄H₉  n ≒ 2~8 | —N(C₄H₉)₂ |

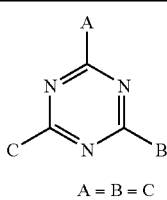

A = B = C

| | |
|---|---|
| b-113 | 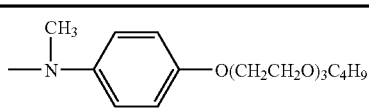 |
| b-114 | 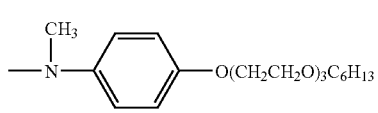 |

The compound represented by formula (2) may be produced according to one or more types of reaction employing cyanuric chloride as a starting material. For example, the compound represented by the formula (2) can be produced by carrying out reaction of trichloro-, dichloro- or monochloro-triazine and amine or aminophenol. The reaction is carried out with release of HCl, and preferably, deoxidizing agent is employed. Base may be employed as a deoxidizing agent. Examples of base employable as a deoxidizing agent include sodium hydroxide, potassium hydroxide, sodium carbonate, potassium carbonate, triethyl amine, N,N-di isopropylethyl amine, 1,8-diaza-bicyclo-[5.4.0]-undece-7-en (DBU), pyridine, N,N-dimethyl aniline, N-methyl morpholine, sodium methoxide and sodium acetate. Among these, for selectively carrying out reaction of the N-position of aminophenol, sodium acetate is preferred as a deoxidizing agent.

Dichloro triazine is a compound formed by replacing one chlorine atom of trichloro triazine with another substituent. Examples of the substituent include alkyl groups (preferably $C_{1-40}$, more preferably $C_{1-20}$ linear or branched alkyl groups); aryl groups such as phenyl and naphthyl; alkoxy groups (preferably $C_{1-40}$ and more preferably $C_{1-20}$ alkoxy groups such as methoxy, ethoxy, methoxyethoxy and phenoxy); mono- and di-alkylamino groups (preferably $C_{1-40}$ and more preferably $C_{1-20}$ mono- and di-alkylamino groups such as butylamino, octylamino, 2-ethylhexylamino, dibutylamino, dioctylamino and di-2-ethylhexylamino), alkyl- and aryl-thio groups (preferably $C_{1-40}$ and more preferably $C_{1-20}$ alkyl thio groups such as methylthio, ethylthio and propylthio; and preferably $C_{6-40}$ and more preferably $C_{6-20}$ arylthio groups such as phenylthio), acyl groups (preferably $C_{1-40}$ and more preferably $C_{2-20}$ acyl groups such as acetyl, propanoyl, octanoyl and benzoyl), acyloxy groups (preferably $C_{1-40}$ and more preferably $C_{2-20}$ acyloxy groups such as acetoxy, pivaloyloxy and benzoylox), alkynyl and alkynyl groups (preferably $C_{2-40}$ and more preferably $C_{6-30}$ linear and branched alkenyl and alkynyl groups); and heterocyclic groups (preferably 5- and 6-membered heterocyclic groups such as pyrrolidine, piperidine and morpholine. These substituents may one or more substituents.

Monochloro triazine is a compound formed by replacing two chlorine atoms of trichloro triazine with other substituents. The two substituents may be same with or different from each other. Examples of the substituent are same as those exemplified as a substituent of dichloro triazine.

Amine employable is a primary or secondary aliphatic amine. Examples of amine include linear or branched (preferably $C_{1-40}$ and more preferably $C_{1-20}$) primary and secondary alkyl amines (secondary amines may have same or different alkyls); and cycloalkyl (preferably 3 to 6 membered cycloalkyl such as cyclopropyl and cyclohexyl) amines.

Aminophenol is a non-substituted aminophenol or alkylaminophenol having an alkyl group at the N-position. The alkyl group is preferably a $C_{1-10}$, more preferably $C_{1-5}$ and even more preferably $C_{1-3}$ alkyl group.

One example of the method for producing the compound represented by formula (2) comprises a step represented by a reaction formula (1) or (II). In the reaction formulae, $R^{10}$ represents a $C_{1-3}$ alkyl group; and $R^{11}$ and $R^{12}$ each represent a substituted or non-substituted linear or branched $C_{1-30}$ alkyl group.

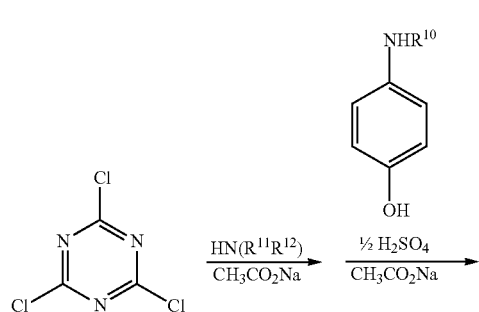
(I)

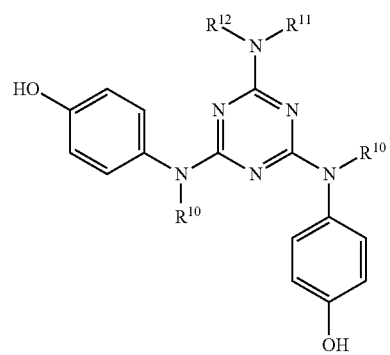

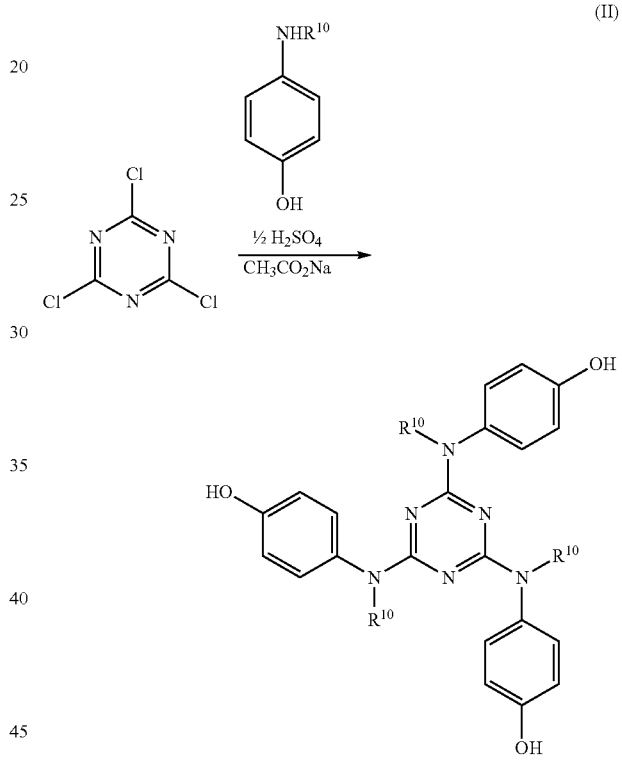
(II)

Further, OH in the compound may be converted into OR by carrying out any reaction. R is a substituent, and preferable examples of R include any substituents containing at least one linear or branched alkyl chain having the total number of carbon atoms equal to or greater than 8, linear or branched oligoalkyleneoxy chain having the total number of the carbon atoms equal to or greater than 4, linear or branched perfluoroalkyl chain having the total number of carbon atoms equal to or greater than 2, or linear or branched perfluoroalkylether chain having the total number of carbon atoms equal to or greater than 2, or linear or branched organic polysiloxyl chain. According to the method, which is simple, it is possible to produce compounds represented by formula (2), in which at least one of $R^{11}$—$X^{11}$, $R^{12}$—$X^{12}$ and $R^{13}$—$X^{13}$ is a group represented by formula (3) in a good yield.

Synthetic Examples of Compounds b-116, b-122 and b-44 will be described below.

Synthetic Example of Compound b-116

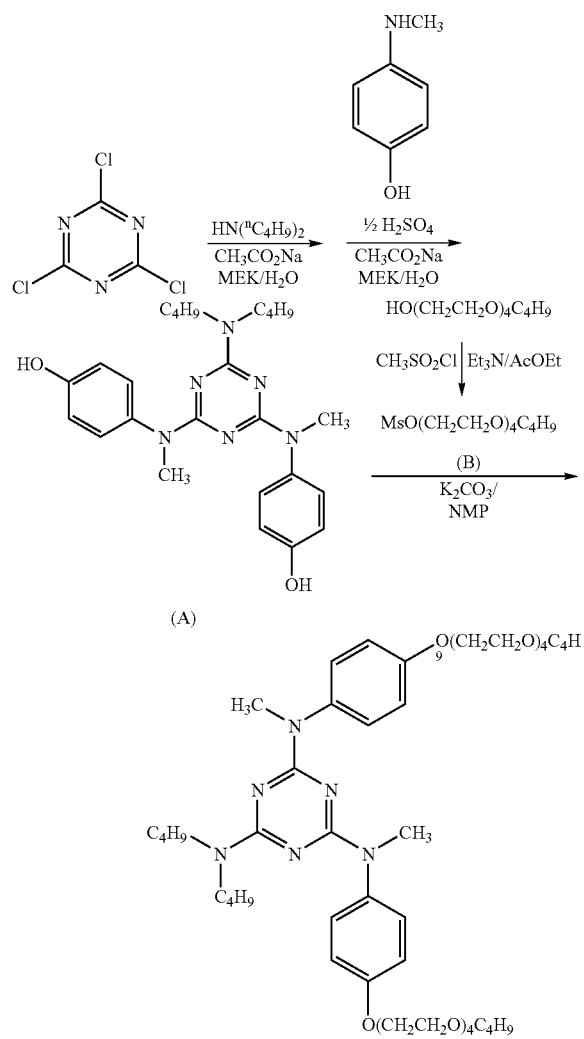

Preparation of Intermediate A:

In 1600 mL of methylethyl ketone (MEK), 232.2 g (1.26 mol) of cyanuric chloride was dissolved, cooled with ices, and added dropwise with 163 g (1.26 mole) of dibutylamine at a temperature equal to or lower than 5 deg C. After that, a solution, prepared by dissolving 113 g of sodium acetate in 250 mL of water, was added dropwise to the reaction solution at a temperature equal to or lower than 5 deg C. After that, the reaction solution was stirred at a room temperature for one hour, added dropwise with 475 g (2.78 mol) of p-methyl aminophenol-sulfate (metol), and added dropwise with a solution, prepared by dissolving 465 g (5.67 mol) sodium acetate in 1000 mL of water, under a nitrogen atmosphere. After that, the reaction solution was stirred at a room temperature for 30 minutes, and refluxed under heating for three hours. After the reaction was terminated, the reaction solution was distilled thereby to remove about a half amount (800 mL around) of MEK therefrom, cooled by 30 deg C., and added with a mixture of 630 mL of methanol and 1260 mL of water with stirring. After that, the reaction solution was added with 630 mL of water and cooled by 15 deg C. Then, the product crystallized from the solution, and the product was separated from the solution by filtration, washed with 300 mL of methanol and 300 mL of water, and dried. Then, 512.3 g of the target product was obtained (the yield through the two steps: 90.3%).

Preparation of Intermediate B:

In 2500 mL of ethyl acetate, 338 g (2.95 mol) of tetraethylene glycol monobutyl ether (produced by Kyowa Hakko Chemical Co., LTD) was dissolved, cooled, added dropwise with 338 g (2.95 mol) of methane sulfonyl chloride at a temperature equal to or lower than 10 deg C., and added with 323.8 g (3.20 mol) of triethyl amine at a temperature equal to or lower than 5 deg C. After that, the reaction solution was stirred at a room temperature for one hour, and extracted and washed with 2000 mL of water three times. The organic layer (ethyl acetate layer) was concentrated under reduced pressure, and then 972 g (yield: 100%) of the target product was obtained.

Preparation of Compound b-116:

In 1500 mL of N-methylpyrrolidone, 512.3 g (1.13 mol) of Intermediate A and 972 g (2.96 mol) of Intermediate B were dissolved, added with 610 g (4.41 mol) of potassium carbonate, and stirred at a temperature from 90 to 100 deg C. for five hours thereby to carry out reaction of them. After the reaction was terminated, the reaction solution was cooled by 25 deg C., added with 2000 mL of water and extracted with 2500 mL of toluene.

After separation, the organic layer (toluene layer) was washed with 2000 mL of water twice, concentrated under reduced pressure, and then 1000 g (yield: 95%) of the target product was obtained.

Synthetic Example of Compound b-122

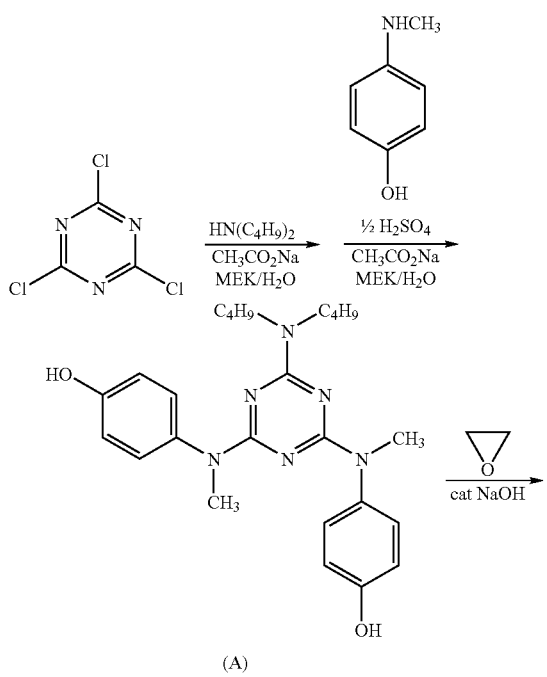

-continued

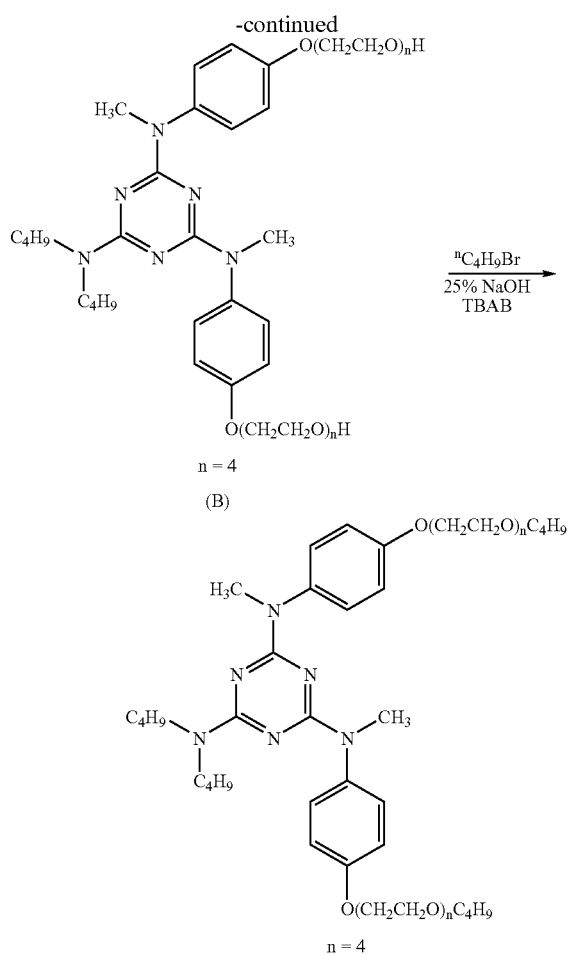

(B)

n = 4

Preparation of Intermediate A:

In 1600 mL of methylethyl ketone (MEK), 232.2 g (1.26 mol) of cyanuric chloride was dissolved, cooled with ices, and added dropwise with 163 g (1.26 mole) of dibutylamine at a temperature equal to or lower than 5 deg C. After that, a solution, prepared by dissolving 113 g (1.38 mol) of sodium acetate in 250 mL of water, was added dropwise to the reaction solution at a temperature equal to or lower than 5 deg C. After that, the reaction solution was stirred at a room temperature for one hour, added dropwise with 475 g (2.78 mol) of p-methyl aminophenol-sulfate (metol), and added dropwise with a solution, prepared by dissolving 465 g (5.67 mol) in 1000 mL of water, under a nitrogen atmosphere. After that, the reaction solution was stirred at a room temperature for 30 minutes, and refluxed under heating for three hours. After the reaction was terminated, the reaction solution was distilled thereby to remove about a half amount (800 mL around) of MEK therefrom, cooled by 30 deg C., and added with a mixture of 630 mL of methanol and 1260 mL of water with stirring. After that, the reaction solution was added with 630 mL of water and cooled by 15 deg C. Then, the product crystallized from the solution, and the product was separated from the solution by filtration, washed with 300 m L of methanol and 300 mL of water, and dried. Then, 512.3 g of the target product was obtained (the yield through the two steps: 90.3%).

Preparation of Intermediate B:

In a vessel, 512.3 g (1.13 mol) of Intermediate A, 2.3 g (0.057 mol) of sodium hydroxide and an amount corresponding to 9.04 mol of oxidation ethylene gas were enclosed, and reacted at 120 deg C. for five hours. After the reaction was terminated, the reaction product was cooled by a room temperature, and dissolved in 3000 mL of ethyl acetate. The organic layer was washed with 2000 mL of water twice. After extraction, the organic layer was concentrated under reduced pressure, and then 816 g (yield: 90%) of the target product was obtained.

Preparation of Compound b-122 (n is nearly equal to 4):

In a vessel, 816 g (1.02 mol) of Intermediate B, 1398 g (10.2 mol) of n-butyl bromide, 1632 g (10.2 mol) of 25% sodium hydroxide solution and 32.9 g (0.102 mol) of tetrabutyl ammonium bromide (TBAB) were enclosed, and reacted at a temperature from 65 to 70 deg C. for five hours. After the reaction was terminated, the reaction product was cooled by 25 deg C., dissolved in 3000 mL of toluene and washed with 1500 mL of water three times. After washing, the organic layer was concentrated under reduced pressure, and then 914.8 g (yield: 98%) of the target product was obtained.

Synthetic Example of Compound b-44

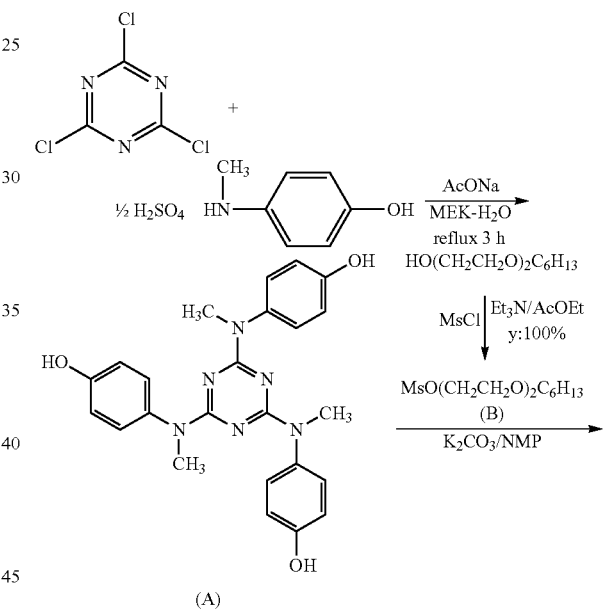

(A)

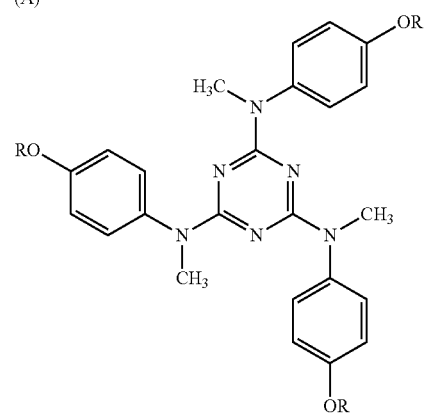

$R = -(CH_2CH_2O)_2C_6H_{13}$

Preparation of Intermediate A:

In 1360 mL of methylethyl ketone (MEK), 170 g (0.92 mol) of cyanuric chloride was dissolved, cooled, and added with 525.6 g (3.04 mol) of p-methyl aminophenol-sulfate (metol) at a temperature equal to or lower than 5 deg C., and added dropwise with a solution, prepared by dissolving 501.2 g (6.12 mol) of sodium acetate in 1100 mL of water under a nitrogen atmosphere. After that, the reaction solution was refluxed for three hours, and distilled under a normal pressure thereby to remove MEK therefrom, cooled by 30 deg C., added with a mixture of 340 mL of acetone and 1360 mL of water and stirred at a temperature equal to or lower than 5 deg C. for one hour. Then, the product crystallized from the solution, and the product was separated from the solution by filtration, washed with a mixture of 170 mL of acetone and 680 mL of water, and dried. Then, 391 g (yield: 95%) of the target product was obtained.

Preparation of Intermediate B:

In 3400 mL of ethyl acetate, 641.2 g (3.37 mol) of diethylene glycol monohexyl ether was dissolved, cooled, added dropwise with 405 g (3.55 mol) of methane sulfonyl chloride at a temperature equal to or lower than 10 deg C., and added with 376 g (3.71 mol) of triethyl amine at a temperature equal to or lower than 10 deg C. After that, the reaction solution was stirred at a room temperature for one hour, and extracted and washed with 1000 mL of water three times. The organic layer (ethyl acetate layer) was concentrated under reduced pressure, and then 904 g (yield: 100%) of the target product was obtained.

Preparation of Compound b-44:

In 1500 mL of N-methylpyrrolidone, 411.4 g (0.92 mol) of Intermediate A and 904 g (3.37 mol) of Intermediate B were dissolved, added with 513 g (3.37 mol) of potassium carbonate, and stirred at a temperature from 90 to 100 deg C. for five hours thereby to carry out reaction of them. After the reaction was terminated, the reaction solution was cooled by 25 deg C., added with 3000 mL of water, and extracted with 3000 mL of toluene.

After separation, the organic layer (toluene layer) was washed with 2000 mL of water twice, concentrated under reduced pressure, and then 961.3 g (yield: 95%) of the target product was obtained.

Preferably, the lubricant composition of the invention comprises from 50.0 to 99.9 mass % of ingredient (a) and from 0.01 to 50 mass % of ingredient (b), and more preferably from 80.0 to 99.9 mass % of ingredient (a) and from 1.0 to 20 mass % of ingredient (b).

Base Oil:

The lubricant composition of the invention may further comprise a base oil. The oily substance (lubricant oil) to be used as a base oil in the lubricant composition may be selected from any mineral oils and synthetic oils having been used for base oil of conventional lubricating oil composition. More specifically the base oil may be selected form synthetic hydrocarbon oils, paraffin-base mineral oils, alkyl diphenyl ether oils, silicone oils, naphthene base oils, polyoxyalkylene and/or polyoxyalkylene ether derivatives, or that is, polyglycol base synthetic oils (disclosed in JAP No. hei 4-266995) and ester oils such as dieters and polyol esters. Synthetic hydrocarbon oils are preferred for sliding faces made of resin material.

Examples of the synthetic hydrocarbon oil include poly-alpha-olefins, ethylene-alpha-olefin oligomers and polybutenes. Secondarily preferred after synthetic hydrocarbon oils are paraffin base mineral oils, alkyl diphenyl ether oils and silicone oils for sliding faces made of resin material. Two or more kinds of oils selected from those may be used.

For example, any of mineral oil, synthetic oil, or mixed oil of them may be used. The mineral oil is exemplified by solvent-purified raffinate obtained by extracting raw material of lubricating oil derived by distillation under normal pressure or reduced pressure of paraffin-base, intermediate-base or naphthene-base crude oil using an aromatic extraction solvent such as phenol, furfural or N-methylpyrrolidone; hydrogen-treated oil obtained by bringing raw material of lubricating oil into contact with hydrogen, under the presence of a hydrogen treatment catalyst such as cobalt or molybdenum held by silica-alumina; hydrocracked oil obtained by bringing the raw material into contact with hydrogen, under the presence of a hydrocracking catalyst under severe conditions for cracking; isomerized oil obtained by bringing wax into contact with hydrogen, under the presence of an isomerization catalyst under conditions for isomerization; and distillation fraction of lubricating oil obtained by combinations of solvent purification process with hydrogen treatment process, hydrocracking process, isomerization process and so forth. In particular, high-viscosity-index mineral oil obtained by the hydrocracking process or isomerization process may be exemplified as a preferable product. In any method of the manufacturing, processes such as dewaxing, hydrofinishing, clay treatment process and so forth may arbitrarily be selectable according to general procedures. Specific examples of mineral oil include light neutral oil, medium neutral oil, heavy neutral oil, bright stock and so forth, wherein the base oil may be prepared by arbitrary mixing these oils so as to satisfy desired performances. The synthetic oil may be exemplified by poly($\alpha$-olefin), $\alpha$-olefin oligomer, polybutene, alkylbenzene, polyol ester, dibasic acid ester, polyoxyalkylene glycol, polyoxyalkylene glycol ether, silicone oil and so forth. These base oils may be used independently, or in combination of two or more species thereof.

On the other hand, hindered ester base synthetic oils have been proposed as lubricant base oil for high viscosity index, good low-temperature fluidity, good thermal oxidation stability, and low volatile. For example, in JPA No. hei 6-158079, an ester-base lubricant oil composition comprising $C_{4-26}$ fatty acid having a side chain at the 2-position, $C_{4-26}$ fatty acid having a side chain at the 3-position, and $C_{4-54}$ fatty acid having no side chain at the 2- or 3-position is disclosed. And in JPA No. hei 7-224289, a synthetic lubricant oil composition comprising pentaerythritol, linear saturated monocarboxylic acid, and alpha-branched saturated carboxylic acid is disclosed. They are employable.

Silicone Oil:

The lubricant composition may comprise a silicone oil as a base oil. Such a lubricant composition may be employed in any lubrication portion, which is required to exhibit not only good anti-wear properties but also good friction properties, such as overrunning clutches in automatic starters, one-way clutches in business equipments and various traction drives. Silicone oil is organopolysiloxane, and is excellent in heat resistance, oxidation stability and viscosity-temperature properties. Modified silicone oils, which may be prepared by replacing a part of substituents of silicone oil with other substituent such as a chlorophenyl, fluoroalkyl, long-chain alkyl and high fatty acid residue, can also be used.

Additives:

In view of ensuring practical performances adaptive to various applications, the lubricant composition of the present invention may optionally be added with various additives generally used for lubricant including bearing oil, gear oil and power transmission oil, that is, anti-wearing agent, extreme pressure agent, antioxidant, viscosity index improver, detergent-dispersant, metal deactivator, anticorrosive, anti-rust agent, defoaming agent, solid lubricant and so forth, within ranges without impairing the purpose of the present invention. The lubricant composition of the present invention may contain a medium for the organic compound. The medium can be selected from any materials so far as they do not inhibit spontaneous formation of the self-organizing material. For example, one species, or two or more species may be selected from general mineral oils and synthetic oils which have conventionally been used as lubricant base oils. It is to be noted that any lubricant compositions containing other ingredients preferably comprise ingredient (a) in an amount of 50 mass % or more, and more preferably 80 mass % or more, with respect to the total mass of the composition.

Applications:

The lubricant composition of the invention can be used in various applications. The lubricant composition may be used, for example, as engine or gear oil for vehicles such as automobiles, operating oil for automobiles, lubricant oil for ships or airplanes, machine oil, turbine oil, bearing oil, hydraulic operating oil, pump oil for compressors or vacuum pumps, refrigerant oil, metalworking oil, lubricant for magnetic recording media, lubricant for micro-machines, or lubricant for artificial bones.

[Mechanical Element]

The present invention relates to a mechanical element comprising at least two surfaces movable at peripheral speeds different from each other, and the lubricant composition of the invention disposed between such two surfaces. The lubricant composition of the invention may be used in any embodiments comprising at least two surfaces movable at peripheral speeds different from each other. The mechanical element of the invention may be selected from any mechanical elements requiring lubricant oil or grease, used in any conventional friction sliding members. The sliding surfaces movable at peripheral speeds different from each other may be curved or flat surfaces, and have a concavo-convex area partially or as a whole. Examples of the mechanical element of the invention include sliding members of any plane bearings and roller bearings. The mechanical element of the invention may further comprise a transmission element(s) such as a wheel, cam, screw and driver. The mechanical element of the invention may further comprise a sealing element(s), and examples of the sealing element include contact sealings such as oil sealings, mechanical sealings and piston rings.

Materials composing two moving surfaces are not specifically limited. The lubricant composition of the present invention is excellent in low friction performance and anti-wearing performance, when applied to any of steel, various metals other than steel, inorganic materials other than metals, organic materials, and composite of these materials.

Examples of steel include carbon steels for machine structural use; alloy steels for machine structural use such as nickel-chromium steel, nickel-chromium-molybdenum steel, chromium steel, chromium-molybdenum steel and aluminum-chromium-molybdenum steel; stainless steel, and maraged steel.

Also various metals other than steel, inorganic materials other than metals, or organic materials may widely be used.

The inorganic materials other than metals, or organic materials may be exemplified by various plastics, ceramics, carbon, and composite of these materials. More specifically, the metal materials other than steel may be exemplified by cast iron, copper/copper-lead/aluminum alloy, casting of these materials, and white metal.

As for the organic materials, the lubricant composition is adoptable to all general-purpose plastics and engineering plastics, exemplified by high-density polyethylene (HDPE), polyamide, polyacetal (POM), polycarbonate, polyethylene terephthalate, polybutylene terephthalate, polybutylene naphthalate, polyphenylene ether, polyphenylene sulfide (PPS), fluorine-containing resin, tetrafluoroethylene resin (PFPE), polyarylate, polyamide-imide (PAI), polyetherimide, polypyromellite imide, polyether ether ketone (PEEK), polysulfone, polyether sulfone, polyimide (PI), polystyrene, polyethylene, polypropylene, phenol resin, AS resin, ABS resin, AES resin, AAS resin, ACS resin, MBS resin, polyvinyl chloride resin, epoxy resin, diallyl phthalate resin, polyester resin, methacryl resin, ABS/polycarbonate alloy and so forth.

These resins compose mold products or resin layer given as various components and members, wherein the lubricant composition is applied to portions where they are brought into contact with other resins or metals. More specifically, the lubricant composition may effectively be adoptable, for example, to sliding portion, bearing and resin gear unit of automotive electric equipment represented by electric power steering, door mirror and so forth; resin gear unit for audio instruments such as radio cassette recorder, VTR, CD player and so forth; resin gear units for office automation equipment represented by printer, copying machine, facsimile and so forth; and contact portions between resin components composing sliding portions inside various automotive actuators and air cylinder, with other resin components or metal materials.

The inorganic materials may be exemplified by ceramics such as silicon carbide, silicon nitride, alumina, zirconia, titanium carbide (TiC), zirconium carbide (ZrC), and titanium nitride (TiN); and carbon materials. The composite of these materials may be exemplified by organic-inorganic composite materials in which plastics are combined with fibers such as glass, carbon or aramid fiber, and cermet which is a composite material of ceramic and metal.

The surfaces having at least a part of which composed of a material other than iron and steel may be a steel surface having at least a part of which covered with a film composed of a metal material other than steel, or a film composed of an inorganic material other than metal, or a film composed of an organic material. The covering film may be exemplified by a magnetic material film such as diamond-like carbon film, and organic or inorganic porous film.

The above-described two surfaces may be configured so that a porous sintered layer is formed at least on one surface of which, and the lubricant composition is impregnated into the porous layer, so as to allow the lubricant composition to be appropriately supplied to the sliding surface during slide operation. The porous film may be composed of any material selected from metal material, organic material and inorganic material. Specific examples of the material include sintered metal; porous ceramics formed by strong bonding of fine particles of calcium zirconate ($CaZrO_3$) and magnesia (MgO); porous glass obtained by allowing silica and boric acid components to thermally cause phase separation; sintered porous moldings of ultra-high-molecular-weight polyethylene powder; fluorine-containing resin-base porous film such as polytetrafluoroethylene film; polysulfone-base porous film typically adoptable to microfilter and so forth; and porous film formed by preliminarily allowing a poor solvent of the moldings and a monomer for forming the moldings to cause phase separation in the process of polymerization.

The metal or metal oxide sintered layer may be exemplified by porous layer formed by sintering powders of copper base, iron base or $TiO_2$ base. The copper-base sintered layer may be obtained typically by placing a mixture of copper powder (88% by mass, for example), tin (10% by mass, for example) and graphite (2% by mass, for example) on a cast iron substrate, compressing the mixture under 250 MPa, and sintering the product in a reductive gas flow at a temperature of typically as high as 770° C. or around for approximately one hour. The iron-base sintered layer may be obtained by placing a mixture of iron powder added with copper powder (3% by mass, for example) and chemical carbon (0.6% by mass) on a cast iron substrate, compressing the mixture under 250 MPa, and sintering the product in a reductive gas flow at a temperature of typically as high as 770° C. or around for approximately one hour. The $TiO_2$ sintered layer may be obtained by placing a mixture of $Ti(OC_8H_{17}\text{-n})$ (33% by mass, for example), fine powder of $TiO_2$ (57% by mass, for example) and PEO (MW=3000) on a cast iron substrate, and sintering the product at 560° C. for 3 hours under UV irradiation.

Materials to be covered with these porous layers are not specifically limited, and may be above-described ceramics, resin and organic-inorganic composite material, and may, of course, be steel.

The covering film such as the above-described diamond-like-carbon film may be formed by surface treatment. Details of the surface treatment are described in "Tribology Handbook", 1st edition (2001), Series B, Chapter 3, "Surface Treatment (in Japanese)", p. 544-574, edited by Japanese Society of Tribologists, all contents of which are adoptable to manufacturing of the mechanical element of the present invention. The surface treatment is generally given for the purpose of improving tribological characteristics through modification of surface, wherein operation of mechanical element often requires not only low friction and low wear but, at the same time, also various characteristics such as low noise, corrosion resistance, chemical stability, heat resistance, dimensional stability, low out-gas, biocompatibility, anti-bacterial performance and so forth, depending on demands of the operational environment. Accordingly, the surface treatment in the present invention is not limited to those aimed at improving the tribological characteristics. Methods of surface treatment include:

1) formation of films of aluminum, copper, silver, gold, chromium, molybdenum, tantalum or alloys of these metals; ceramics such as titanium nitride, chromium nitride, titanium carbide and chromium carbide; and oxides such as aluminum oxide, silicon dioxide, molybdenum silicide, tantalum oxide and barium titanate, by physical vapor deposition such as vacuum evaporation, ion plating, sputtering and ion implantation;

2) formation of films of various metals; carbides such as WC, TiC and $B_4C$; nitrides such as TiN and $Si_3N_4$; borides such as $TiB_2$ and $W_2B_3$; oxides such as $Al_2O_3$ and $ZrO_2$; CrW; Ti-containing amorphous carbon; fluorine-containing carbon; and plasma-polymerized polymer, by chemical vapor deposition with the aid of heat, plasma, light so forth;

3) methods of providing characteristics such as wear resistance, anti-seize property and so forth to the surficial portion, by diffusive covering process (chemical reaction process) such as carburization, nitriding, sulfurizing, boronization and so forth; and 4) formation of films of metal, composite metal and so forth, by plating process such as electro-plating, electroless plating and so forth.

[Method for Producing Lubricant Composition]

The present invention relates to a method for producing the lubricant composition of the invention.

The method of the invention for producing the lubricant composition, comprising:

producing a mixture of at least two kinds of compounds represented by formula (1) as ingredient (a) and/or a mixture of at least two kinds of compounds represented by formula (2) as ingredient (b); and mixing ingredients (a) and (b).

For example, at least one of ingredients (a) and (b) is produced as a mixture of at least two kinds of compounds represented by formula (1) or (2) according to a reaction employing at least two kinds of reagents.

For example, ingredient (a) is a mixture of at least two kinds of compounds represented by formula (1), which have a substituent as at least one of substituents R containing a repeating unit of ethylene oxy ($-CH_2CH_2O-$) or propylene oxy ($-CH_2CH_2CH_2O-$), of which repeating numbers of the unit are different among said at least two kinds of compounds represented by formula (1); and/or ingredient (b) is a mixture of at least two kinds of compounds represented by formula (2), which have a substituent as at least one of substituents $R^{11}$, $R^{12}$ and $R^{13}$ containing a repeating unit of ethylene oxy ($-CH_2CH_2O-$) or propylene oxy ($-CH_2CH_2CH_2O-$), of which repeating numbers of the unit are different among said at least two kinds of compounds represented by formula (2).

Such the lubricant composition may be prepared according to an addition reaction of ethylene oxide or propylene oxide gas, which has a chain length distribution. The chain length distribution is used for preparing a mixture of at least two kinds of compounds represented by formula (1) or (2).

One example of the method comprises a step of introducing a substituent containing an ethylene oxy unit ($-CH_2CH_2O-$) or propylene oxy unit ($-CH_2CH_2CH_2O-$) as at least one of substituents R or at least one of substituents $R^{11}$, $R^{12}$ and $R^{13}$. According to the method, preferably, a mixture of at least two kinds compounds represented by formula (1), which have a substituent containing a repeating unit of ethylene oxy ($-CH_2CH_2O-$) or propylene oxy ($-CH_2CH_2CH_2O$), of which repeating numbers of the unit are different among said at least two kinds of compounds, is prepared by employing the chain length distribution of ethylene oxide or propylene oxide gas. In one example of the method, addition reaction of ethylene oxide or propylene oxide gas is carried out in the presence of a basic catalyst, and, preferably, in the presence of an organic solvent. One example of the method for preparing a mixture of at least two kinds of compounds represented by formula (1) is shown below. In the scheme shown below, the step of introducing a unit of ethylene oxy ($-CH_2CH_2O-$) or propylene oxy ($-CH_2CH_2CH_2O-$) into one $-X-R$ is shown, and other $-X-R$ groups are omitted from the scheme.

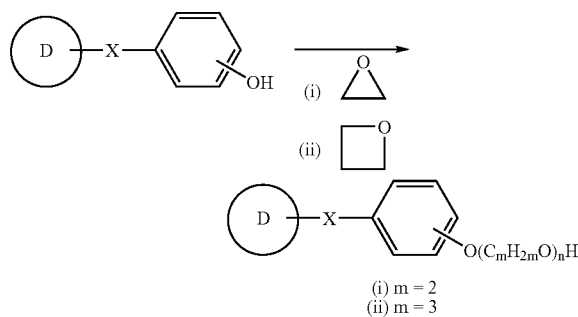

(i) m = 2
(ii) m = 3

The mixture having an average number of "n" from 2 to 4 around may be obtained due to the chain length distribution. If necessary, reaction shown below may be carried out to introduce an alkyl chain ($C_yH_{2y+1}$) at the terminal.

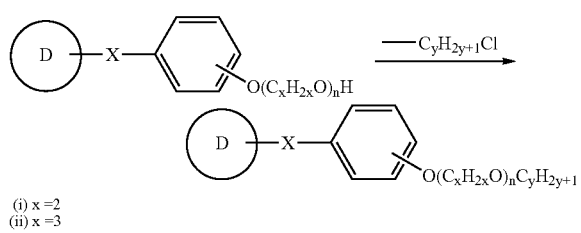

(i) x =2
(ii) x =3

Preferably, the organic solvent which is optionally employed in the reaction system is selected from inactive organic solvents; and examples of such an organic solvent include aromatic hydrocarbon solvents such as benzene, toluene and xylene; ketone solvents such as methyl ethyl ketone and methyl isobutyl ketone; dioxane, ethylene glycol dimethyl ether, dimethyl formamide and dimethyl sulfoxide.

The catalyst which is used in addition reaction of alkylene oxide may be selected from basic catalysts such as alkali metals, alkali metal hydroxides, alkali metal alkoxides and tertiary amines. Alkali metal oxides are preferred in terms of inhibitory effect of byproducts and handleability; and sodium hydroxide oxide and potassium hydroxide are more preferred. The amount of the catalyst is preferably from 0.05 to 0.5 mass % with respect to the mass of the target product.

The reaction temperature is not limited to any range, and reaction may be carried out at a room temperature or under heating. Preferably, reaction is carried out at a temperature from 50 to 150 deg C. The reaction vessel is not limited to any type, and preferably, reaction is carried out in an autoclave.

According to the method of the invention, after reaction is terminated, the obtained reaction mixture may be used without any post-treatment or with any post-treatment for introducing an alkyl group or the like at the terminal as a raw material of the lubricant composition of the invention.

Synthetic Examples of Compound b-97

Compound b-97 was produced according to the scheme shown below.

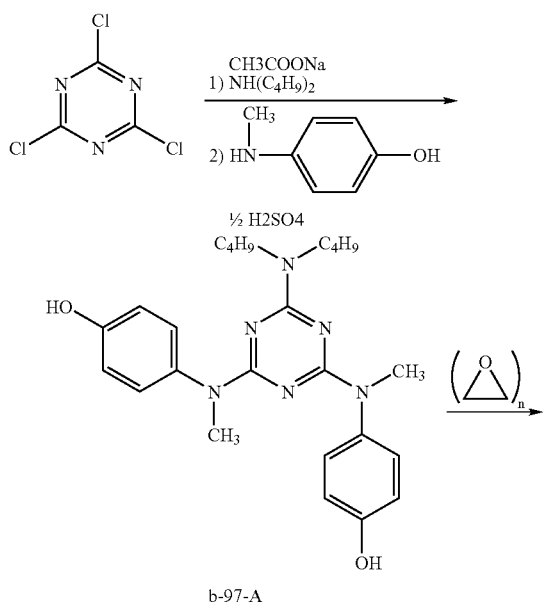

b-97-A

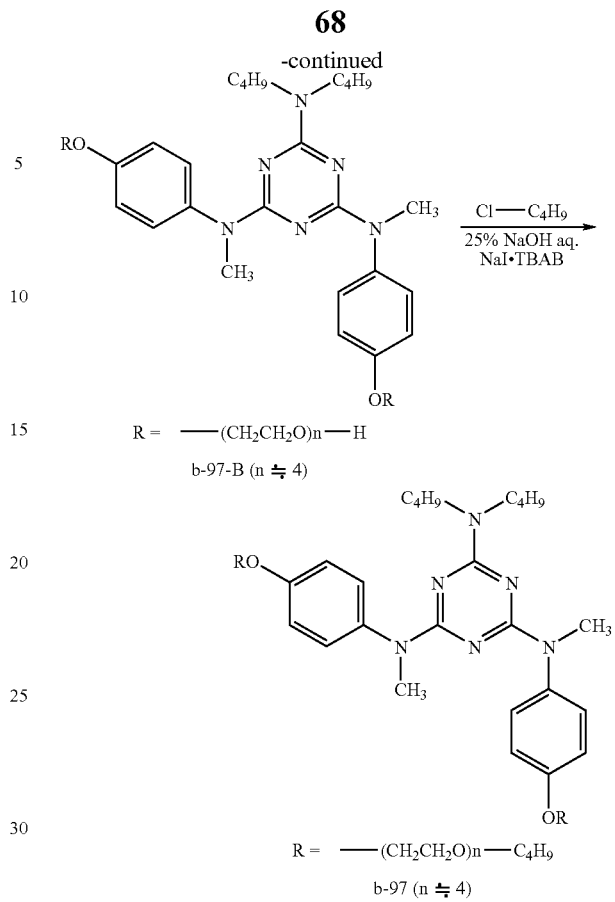

R = —(CH$_2$CH$_2$O)n—H
b-97-B (n ≒ 4)

R = —(CH$_2$CH$_2$O)n—C$_4$H$_9$
b-97 (n ≒ 4)

(Preparation of Compound b-97-A)

In a 1 L three-necked flask provided with a stirring machine, 1.0 mol of cyanuric chloride and 250 mL of methyl ethyl ketone were enclosed, and stirred thereby to give a solution. The solution was cooled by 5 deg C., and added dropwise with 1.0 mol of dibutylamine with stirring. After that, the solution was added dropwise with 100 ml aqueous solution of 1.0 mol sodium acetate, and stirred for two hours. Subsequently, the reaction solution was added with 1.0 mol of metol, and added dropwise with 200 mL of aqueous solution of 2.0 mol of sodium acetate. After the addition was completed, the reaction solution was refluxed for five hours for reacting them. After the reaction was terminated, the solution was extracted with ethyl acetate, washed with water, and the separated organic layer was distilled under reduced pressure thereby to remove solvent therefrom. The product crystallized from methanol-water mixed solvent and the target product, Compound b-97-A, was obtained.

(Preparation of Compound b-97-B)

In an autoclave, 1.0 mol of Compound b-97-A was enclosed, added with 0.5 g of potassium hydroxide powder as a catalyst, and the atmosphere in the autoclave was replaced with nitrogen gas. Into the autoclave, ethylene oxide was pressed, and addition reaction was carried out with stirring at a reaction temperature from 130 to 140 deg C. After maturing for five hours, the content was extracted from the autoclave and washed with water, and then the target product, Compound b-97-B, was obtained.

(Preparation of Compound b-97)

In a 500 mL three-necked flask provided with a stirring machine, 0.5 mol of Compound b-97-B, 200 mL of water, 2.0 mol of sodium hydroxide, and sodium iodide and tetrabutyl ammonium bromide as a catalyst were enclosed, and stirred thereby to give a solution. The solution was added dropwise with 2.0 mol of butyl chloride with stirring. After the addition was completed, the reaction solution was stirred at 65 deg C. for four hours. After the reaction was terminated, the reaction solution was extracted with ethylene acetate, and washed with water. The separated organic layer was distilled under reduced pressure thereby to remove solvent therefrom and then the target product, Compound b-97, was obtained.

EXAMPLES

The invention will be further specifically described below with reference to the following Examples. Materials, reagents, amounts and proportions thereof, operations, and the like as shown in the following Examples can be properly changed so far as the gist of the invention is not deviated. Accordingly, it should not be construed that the scope of the invention is limited to the following specific examples.

Lubricant compositions of Example Nos. 1 to 20 and Comparative Example Nos. 1 to 10, in the tables shown below, were prepared by employing any one of Compounds a-1 to a-4 as ingredient (a) and Compounds b-7, b-12, b-47, b-89, b-97 or b-102 as ingredient (b).

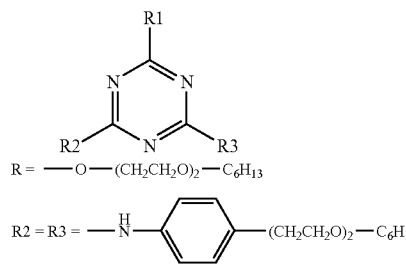
(a-1)

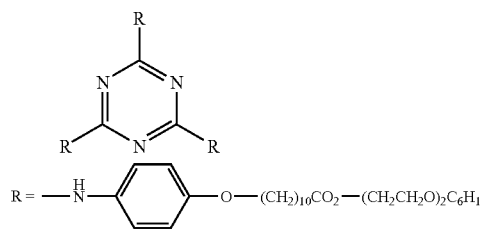
(a-2)

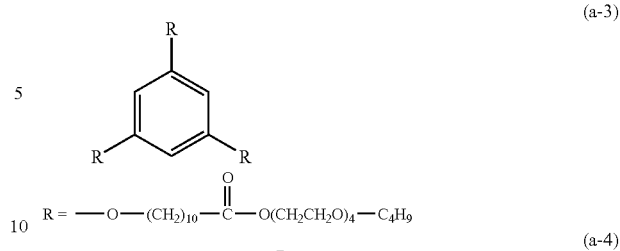
(a-3)

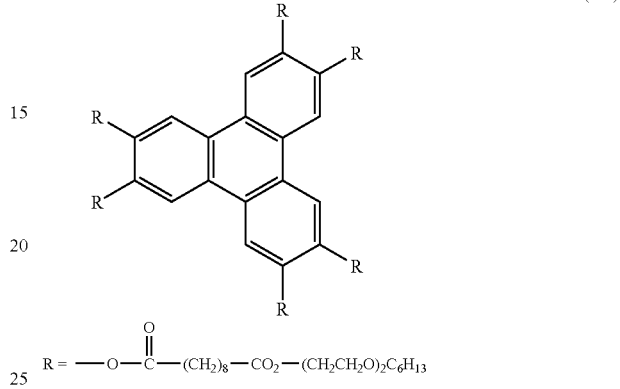
(a-4)

The friction coefficients of the compositions were measured according to a friction test carried out under a condition described below. It is to be noted that each friction coefficient was measured by using a reciprocating type friction test machine (SRV friction wear test machine).

[Friction Coefficient Test Condition]

| Tests were subjected under Cylinder on Plate Test. | |
|---|---|
| Specimen (friction material): | SUJ-2 |
| Plate: | 24 mm in diameter, 6.9 mm thick |
| Cylinder: | 15 mm in diameter, 22 mm long |
| Temperature: | 20 deg C. or 60 deg C. |
| Load: | 20 N or 200 N |
| Amplitude: | 1.5 mm |
| Frequency: | 50 Hz |
| Testing period: | for 10 min. after the start of testing |

TABLE 1

| Compound mas. % | Ex. 1 | Ex. 2 | Ex. 3 | Ex. 4 | Ex. 5 | Ex. 6 | Ex. 7 | Ex. 8 |
|---|---|---|---|---|---|---|---|---|
| a-1 | 40 | — | — | — | 50 | — | — | — |
| a-2 | — | 30 | — | — | — | 50 | — | — |
| a-3 | — | — | 50 | — | — | — | 50 | — |
| a-4 | — | — | — | 20 | — | — | — | 50 |
| b-7 | 60 | — | 50 | — | 25 | — | — | — |
| b-12 | — | 70 | — | — | — | 30 | 10 | 25 |
| b-47 | — | — | — | 80 | 25 | 20 | 40 | 25 |
| Paraffin based MO | — | — | — | — | — | — | — | — |
| Naphthene based MO | — | — | — | — | — | — | — | — |
| PAO | — | — | — | — | — | — | — | — |
| Flow point (° C.) | −45.0 | −38.0 | −55.0 | −39.5 | −45.0 | −40.0 | −55.0 | −47.0 |
| Viscosity (mPa·s) at 40 deg C. | 240 | 230 | 100 | 360 | 220 | 300 | 95 | 280 |
| Test 1*[1] Friction coefficient | 0.08 | 0.08 | 0.08 | 0.08 | 0.08 | 0.08 | 0.08 | 0.08 |

TABLE 1-continued

| Compound mas. % | Ex. 1 | Ex. 2 | Ex. 3 | Ex. 4 | Ex. 5 | Ex. 6 | Ex. 7 | Ex. 8 |
|---|---|---|---|---|---|---|---|---|
| Test 2*[2] Friction Coefficient | 0.05 | 0.05 | 0.05 | 0.05 | 0.06 | 0.06 | 0.06 | 0.06 |

*[1]SRV Frictional Wear Test 1 at 20N and 20° C.
*[2]SRV Frictional Wear Test 1 at 200N and 60° C.

TABLE 2

| Compound mas. % | Ex. 9 | Ex. 10 | Ex. 11 |
|---|---|---|---|
| a-1 | 40 | — | 40 |
| a-2 | — | 30 | — |
| a-3 | — | — | — |
| a-4 | — | — | — |
| b-89 | 60 | — | — |
| b-97 | — | 70 | — |
| b-102 | — | — | 60 |
| Paraffin based MO | — | — | — |
| Naphthene based MO | — | — | — |
| PAO | — | — | — |
| Flow point (° C.) | −45.0 | −50.0 | −45.0 |
| Viscosity (mPa·s) at 40 deg | 140 | 120 | 150 |
| Test 1*[1] Friction coefficient | 0.08 | 0.08 | 0.08 |
| Test 2*[2] Friction Coefficient | 0.05 | 0.05 | 0.05 |

*[1]SRV Frictional Wear Test 1 at 20N and 20° C.
*[2]SRV Frictional Wear Test 1 at 200N and 60° C.

TABLE 4

| Compound mas. % | Com. Ex. 8 | Com. Ex. 9 | Com. Ex. 10 |
|---|---|---|---|
| a-1 | — | — | — |
| a-2 | — | — | — |
| a-3 | — | — | — |
| a-4 | — | — | — |
| b-7 | — | — | — |
| b-12 | — | — | — |
| b-47 | — | — | — |
| Paraffin based MO | 100 | — | — |
| Naphthene based MO | — | 100 | — |
| PAO | — | — | 100 |
| Flow point (° C.) | −25.0 | −10.0 | −50.0 |
| Viscosity (mPa·s) at 40 deg | 46 | 60 | 32 |
| Test 1*[1] Friction coefficient | 0.16 | 0.16 | 0.16 |
| Test 2*[2] Friction Coefficient | 0.16 | 0.15 | 0.17 |

*[1]SRV Frictional Wear Test 1 at 20N and 20° C.
*[2]SRV Frictional Wear Test 1 at 200N and 60° C.

TABLE 3

| Compound mas. % | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|
| a-1 | 100 | — | — | — | — | — | — |
| a-2 | — | 100 | — | — | — | — | — |
| a-3 | — | — | 100 | — | — | — | — |
| a-4 | — | — | — | 100 | — | — | — |
| b-7 | — | — | — | — | 100 | — | — |
| b-12 | — | — | — | — | — | 100 | — |
| b-47 | — | — | — | — | — | — | 100 |
| Paraffin based MO | — | — | — | — | — | — | — |
| Naphthene based MO | — | — | — | — | — | — | — |
| PAO | — | — | — | — | — | — | — |
| Flow point (° C.) | −25.0 | −10.0 | −50.0 | −7.0 | −32.0 | −35.5 | −35.9 |
| Viscosity (mPa·s) at 40 deg | 390 | 1000 | 120 | 400 | 260 | 220 | 350 |
| Test 1*[1] Friction coefficient | 0.13 | 0.12 | 0.12 | 0.13 | 0.09 | 0.09 | 0.10 |
| Test 2*[2] Friction Coefficient | 0.06 | 0.05 | 0.07 | 0.05 | 0.07 | 0.07 | 0.07 |

*[1]SRV Frictional Wear Test 1 at 20N and 20° C.
*[2]SRV Frictional Wear Test 1 at 200N and 60° C.

From the results shown in the tables, it is understandable that the examples of the invention exhibited a low friction coefficient under both of conditions of a relatively-low temperature and pressure and a relatively-high temperature and pressure. It is also understandable that the flow point can be decreased by combining ingredients (a) and (b), and that the examples of the invention exhibited low-temperature properties.

The invention claimed is:

1. A lubricant composition comprising following ingredients (a) and (b):
   (a) at least one compound represented by formula (1)

(R—X—)$_m$-D     (1)

where "D" represents an m-valent cyclic group capable of bonding to "m" of —X—R; X each independently represents a single bond or a bivalent linking group selected from the group consisting of NH, an oxygen atom, a sulfur atom, carbonyl, sulfonyl and any combinations thereof; R each independently represents a substituted or non-substituted alkyl group, alkenyl group, alkynyl group, aryl group or heterocyclic group, or a halogen atom, hydroxy, mercapto, cyano, sulfide, carboxy or a salt thereof, sulfo or a salt thereof, hydroxyamino, ureido or urethane; and m is an integer from 2 to 11;
   (b) at least one compound represented by formula (2)

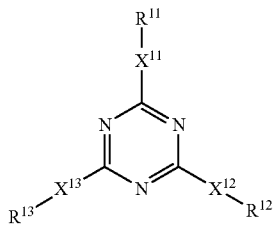

(2)

where $X^{11}$, $X^{12}$ and $X^{13}$ each independently represent a single bond or a bivalent linking group selected from the group consisting of $NR^a$ (where $R^a$ is a hydrogen atom or a $C_{1-30}$ alkyl group), an oxygen atom, a sulfur atom, carbonyl, sulfonyl and any combinations thereof, provided that at least one of $X^{11}$, $X^{12}$ and $X^{13}$ represents $NR^b$ (where $R^b$ represents a $C_{1-30}$ alkyl group); and $R^{11}$, $R^{12}$ and $R^{13}$ each independently a substituted or non-substituted alkyl group, alkenyl group, alkynyl group, aryl group or heterocyclic group.

2. The lubricant composition of claim 1, wherein "D" in formula (1) is a cyclic group represented by any one of formulae [1] to [74]:

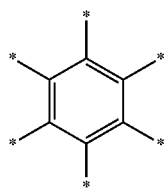
[1]

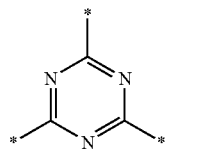
[2]

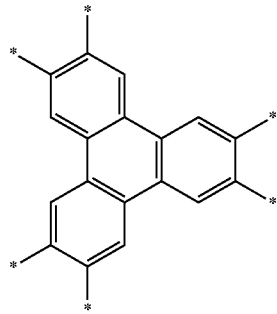
[3]

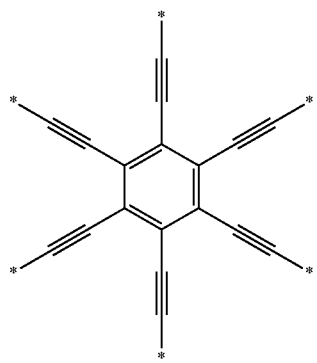
[4]

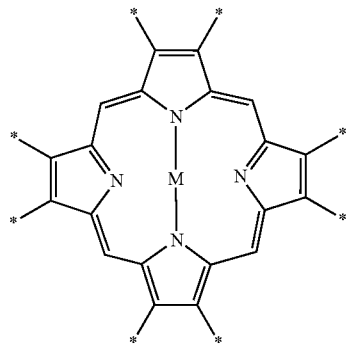
[5]

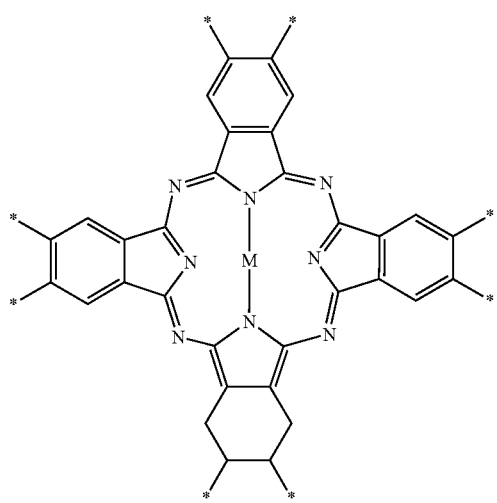
[6]

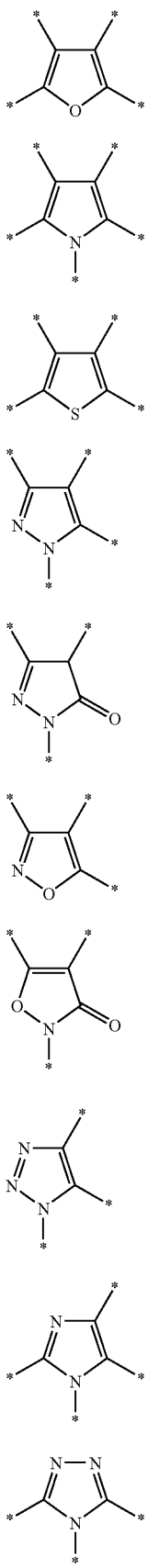
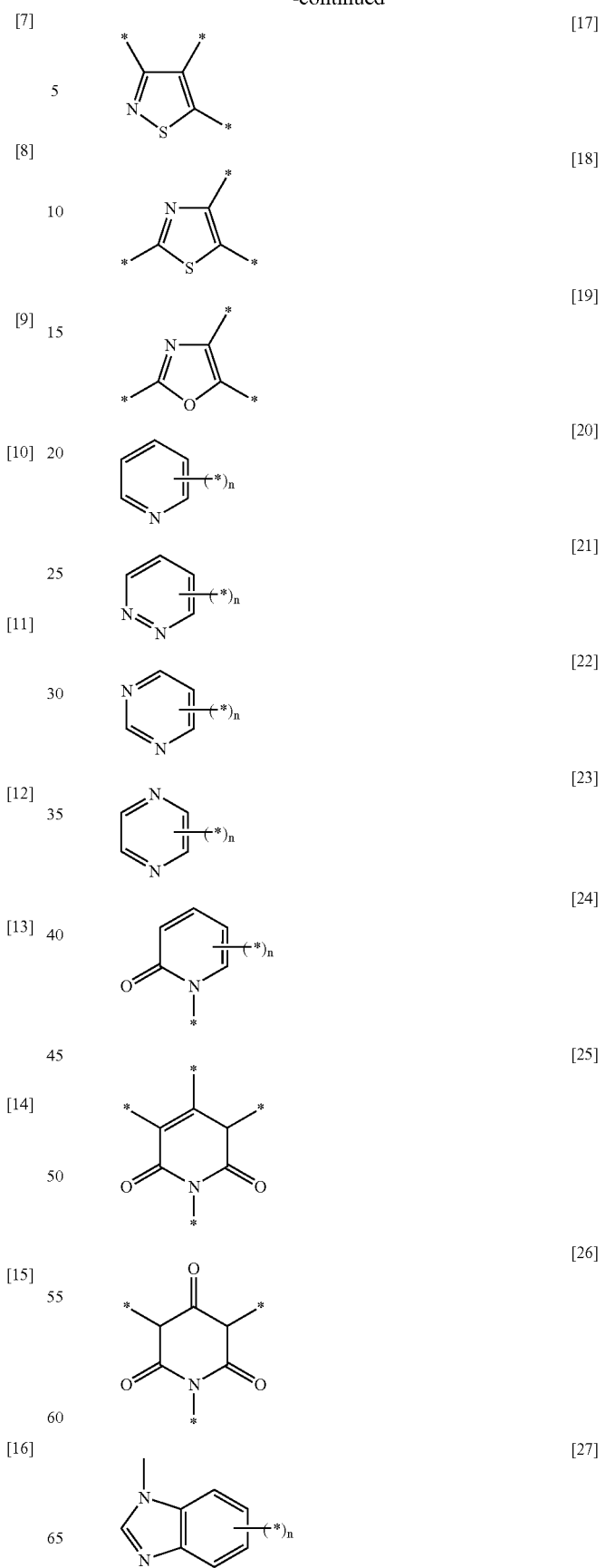

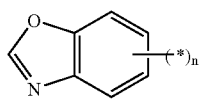
[28]
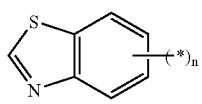
[29]
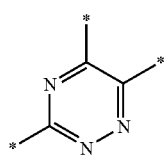
[30]
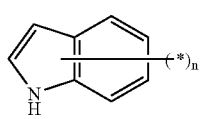
[31]
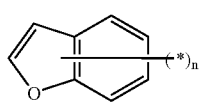
[32]
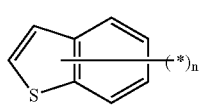
[33]
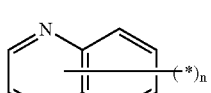
[34]
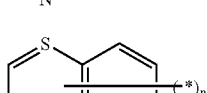
[35]
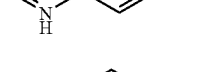
[36]
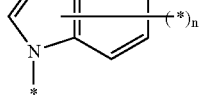
[37]
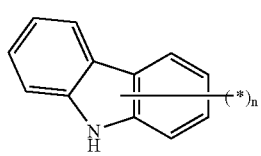
[38]
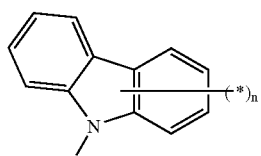
[39]
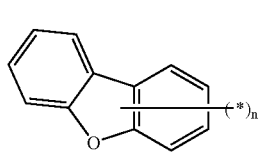
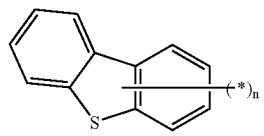
[40]
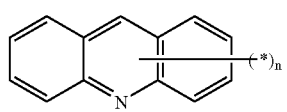
[41]
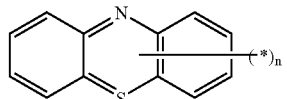
[42]
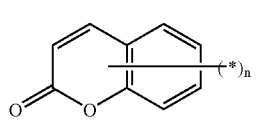
[43]
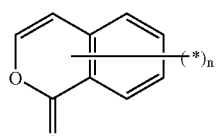
[44]
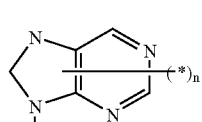
[45]
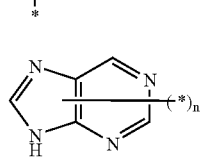
[46]
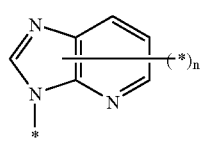
[47]
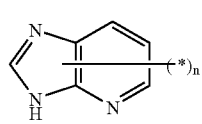
[48]
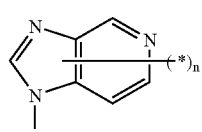
[49]
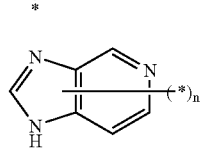
[50]
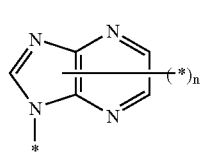
[51]

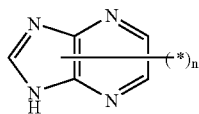 [52]
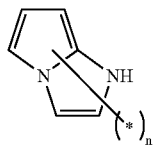 [53]
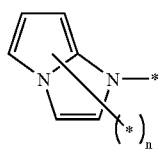 [54]
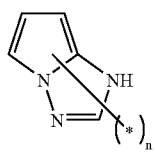 [55]
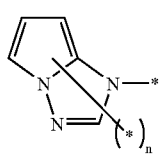 [56]
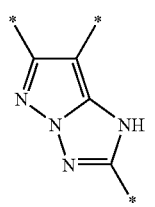 [57]
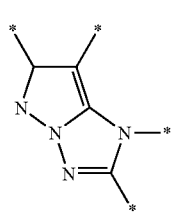 [58]
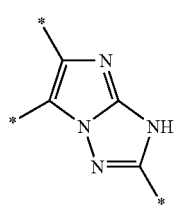 [59]
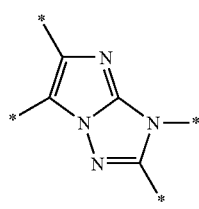 [60]
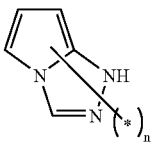 [61]
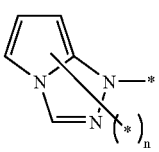 [62]
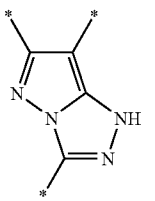 [63]
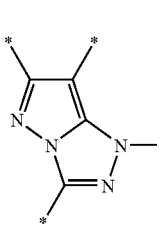 [64]
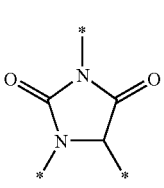 [65]
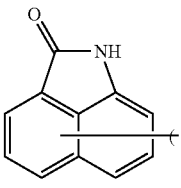 [66]
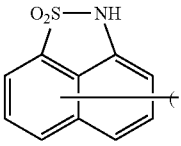 [67]
[68]
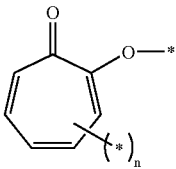 [69]

-continued

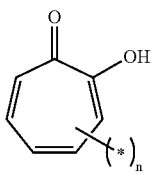

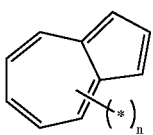

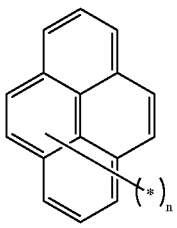

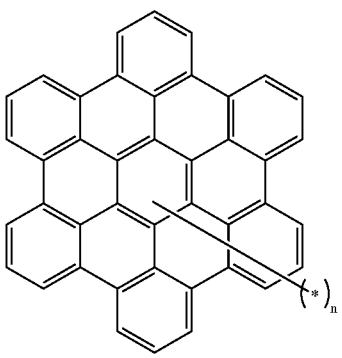

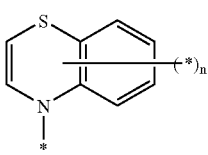

where n is a integer equal to or more than 2; each * in the formulae means a site bindable with a side chain, provided that all portions indicated with * are not necessary to bind to a side chain; and M represents a metal ion or two hydrogen atoms.

3. The lubricant composition of claim 1, wherein "D" in formula (1) is a 5-, 6- or 7-membered heterocyclic ring residue.

4. The lubricant composition of claim 1, wherein at least one of $R^{11}$—$X^{11}$, $R^{12}$—$X^{12}$ and $R^{13}$—$X^{13}$ in formula (2) is a group represented by formula (3):

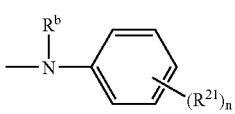

(3)

where $R^b$ represents a $C_{1-30}$ alkyl group; $R^{21}$ represents a substituted or non-substituted alkyl group, alkenyl group, alkynyl group, aryl group or heterocyclic group; and n is an integer from 1 to 5.

5. The lubricant composition of claim 4, wherein $R^b$ in formula (3) is a $C_{1-3}$ alkyl group.

6. The lubricant composition of claim 1, comprising 5.0 to 90.0% by mass of said ingredient (a) and 10.0 to 95.0% by mass of said ingredient (b).

7. The lubricant composition of claim 1, comprising two or more compounds represented by formula (2).

8. A mechanical element comprising at least two surfaces movable at peripheral speeds differed from each other, and a lubricant composition as set forth in claim 1 disposed between said two surfaces.

9. A method for reducing friction between two surfaces, comprising providing a lubricant composition as set forth in claim 1 to a gap between two faces.

10. A method for producing a lubricant composition as set forth in claim 1, comprising:
producing a mixture of at least two kinds of compounds represented by formula (1) as ingredient (a) and/or a mixture of at least two kinds of compounds represented by formula (2) as ingredient (b); and
mixing ingredients (a) and (b).

11. The method of claim 10, wherein at least one of ingredients (a) and (b) is produced as a mixture of at least two kinds of compounds represented by formula (1) or (2) according to a reaction employing at least two kinds of reagents.

12. The method of claim 10, wherein at least one of ingredients (a) and (b) is produced according to an addition reaction of ethylene oxide or propylene oxide gas, which has a chain length distribution, as a mixture of at least two kinds of compounds represented by formula (1) or (2).

13. A lubricant composition comprising following ingredients (a) and (b):
(a) at least one compound represented by formula (1)

$$(R-X-)_m-D \qquad (1)$$

where "D" represents an m-valent cyclic group capable of bonding to "m" of —X—R; X each independently represents a single bond or a bivalent linking group selected from the group consisting of NH, an oxygen atom, a sulfur atom, carbonyl, sulfonyl and any combinations thereof; R each independently represents a substituted or non-substituted alkyl group, alkenyl group, alkynyl group, aryl group or heterocyclic group, or a halogen atom, hydroxy, mercapto, cyano, sulfide, carboxy or a salt thereof, sulfo or a salt thereof, hydroxyamino, ureido or urethane; and m is an integer from 2 to 11;
(b) at least one compound represented by formula (2)

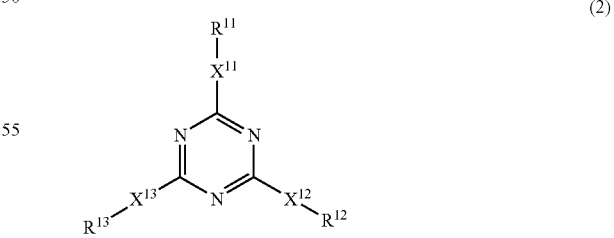

where $X^{11}$, $X^{12}$ and $X^{13}$ each independently represent a single bond or a bivalent linking group selected from the group consisting of $NR^a$ (where $R^a$ is a hydrogen atom or a $C_{1-30}$ alkyl group), an oxygen atom, a sulfur atom, carbonyl, sulfonyl and any combinations thereof, provided that at least one of $X^{11}$, $X^{12}$ and $X^{13}$ represents $NR^b$ (where $R^b$ represents a $C_{1-30}$ alkyl group); and $R^{11}$, R¹² and R¹³ each independently a substituted or non-substituted alkyl group, alkenyl group, alkynyl group, aryl group or heterocyclic group, and
produced according to a method as set forth in claim 10,
wherein at least one of ingredients (a) and (b) is a mixture of at least two kinds of compounds represented by formula (1) or (2).

14. The lubricant composition of claim 13, wherein ingredient (a) is a mixture of at least two kinds of compounds represented by formula (1), which have a substituent as at least one of substituents R containing a repeating unit of ethylene oxy or propylene oxy, of which repeating numbers of the unit are different among said at least two kinds of compounds represented by formula (1); and/or ingredient (b) is a mixture of at least two kinds of compounds represented by formula (2), which have a substituent as at least one of substituents $R^{11}$, $R^{12}$ and $R^{13}$ containing a repeating unit of ethylene oxy or propylene oxy, of which repeating numbers of the unit are different among said at least two kinds of compounds represented by formula (2).

15. A method for producing a mixture of at least two kinds of compounds represented by formula (1):

(1)

where "D" represents an m-valent cyclic group capable of bonding to "m" of —X—R; X each independently represents a single bond or a bivalent linking group selected from the group consisting of NH, an oxygen atom, a sulfur atom, carbonyl, sulfonyl and any combinations thereof; R each independently represents a substituted or non-substituted alkyl group, alkenyl group, alkynyl group, aryl group or heterocyclic group, or a halogen atom, hydroxy, amino, mercapto, cyano, sulfide, carboxy or a salt thereof, sulfo or a salt thereof, hydroxyamino, ureido or urethane, provided that at least one of R is a substituent containing a repeating unit of ethylene oxy or propylene oxy; and m is an integer from 2 to 11;

comprising carrying out addition reaction of ethylene oxide or propylene oxide gas which has a chain length distribution, thereby to form a mixture of at least two kinds of compounds represented by formula (1), which have a substituent containing a repeating unit of ethylene oxy or propylene oxy, of which repeating numbers of the unit are different among said at least two kinds of compounds.

16. A method for producing a mixture of at least two kinds of compounds represented by formula (2):

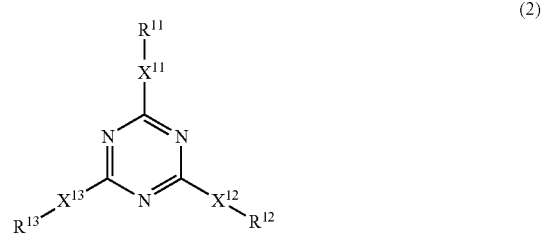

(2)

where $X^{11}$, $X^{12}$ and $X^{13}$ each independently represent a single bond or a bivalent linking group selected from the group consisting of $NR^a$ (where $R^a$ is a hydrogen atom or a $C_{1-30}$ alkyl group), an oxygen atom, a sulfur atom, carbonyl, sulfonyl and any combinations thereof, provided that at least one of $X^{11}$, $X^{12}$ and $X^{13}$ represents $NR^b$ (where $R^b$ represents a $C_{1-30}$ alkyl group); and $R^{11}$, $R^{12}$ and $R^{13}$ each independently a substituted or non-substituted alkyl group, alkenyl group, alkynyl group, aryl group or heterocyclic group, provided that at least one of $R^{11}$, $R^{12}$ and $R^{13}$ is a substituent containing a repeating unit of ethylene oxy or propylene oxy;

comprising carrying out addition reaction of ethylene oxide or propylene oxide gas which has a chain length distribution, thereby to form a mixture of at least two kinds of compounds represented by formula (2), which have a substituent containing a repeating unit of ethylene oxy or propylene oxy, of which repeating numbers of the unit are different among said at least two kinds of compounds.

\* \* \* \* \*